US008877901B2

(12) United States Patent
Govindan

(10) Patent No.: US 8,877,901 B2
(45) Date of Patent: Nov. 4, 2014

(54) CAMPTOTHECIN-BINDING MOIETY CONJUGATES

(75) Inventor: Serengulam V. Govindan, Summit, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 603 days.

(21) Appl. No.: 11/388,032

(22) Filed: Mar. 23, 2006

(65) Prior Publication Data

US 2006/0193865 A1 Aug. 31, 2006

Related U.S. Application Data

(63) Continuation-in-part of application No. 10/734,589, filed on Dec. 15, 2003, now Pat. No. 7,585,491.

(60) Provisional application No. 60/433,017, filed on Dec. 13, 2002, provisional application No. 60/668,603, filed on Apr. 6, 2005, provisional application No. 60/728,292, filed on Oct. 19, 2005, provisional application No. 60/751,196, filed on Dec. 16, 2005.

(51) Int. Cl.

| | |
|---|---|
| ***C07K 16/00*** | (2006.01) |
| ***C07K 16/28*** | (2006.01) |
| ***A61K 47/48*** | (2006.01) |
| ***C07K 16/10*** | (2006.01) |
| ***C07K 16/30*** | (2006.01) |
| *A61K 39/00* | (2006.01) |

(52) U.S. Cl.

CPC ....... *C07K 16/2803* (2013.01); *A61K 47/48384* (2013.01); *A61K 47/4853* (2013.01); *A61K 47/48561* (2013.01); *A61K 47/48715* (2013.01); *C07K 16/1063* (2013.01); *C07K 16/2833* (2013.01); *C07K 16/2863* (2013.01); *C07K 16/30* (2013.01); *A61K 2039/505* (2013.01)

USPC .................. 530/391.9; 530/391.7; 530/391.1; 530/387.1; 530/387.3

(58) Field of Classification Search

USPC ...................................................... 530/387.3

See application file for complete search history.

(56) References Cited

U.S. PATENT DOCUMENTS

| | | | | |
|---|---|---|---|---|
| 4,359,457 | A | 11/1982 | Neville, Jr. et al. | |
| 5,112,954 | A | 5/1992 | Abrams et al. | |
| 5,708,146 | A | 1/1998 | Willner et al. | |
| 5,824,701 | A | 10/1998 | Greenwald et al. | |
| 6,214,345 | B1 * | 4/2001 | Firestone et al. | 424/178.1 |
| 6,310,261 | B1 | 10/2001 | Geissler et al. | |
| 6,716,821 | B2 | 4/2004 | Zhao et al. | |
| 7,550,633 | B2 | 6/2009 | Friedrich et al. | |
| 7,591,994 | B2 * | 9/2009 | Govindan et al. | 424/1.49 |
| 7,999,083 | B2 * | 8/2011 | Govindan et al. | 530/391.7 |
| 2001/0034363 | A1 | 10/2001 | Li et al. | |
| 2003/0133972 | A1 | 7/2003 | Danthi et al. | |
| 2004/0001838 | A1 * | 1/2004 | Zhao et al. | 424/178.1 |
| 2006/0074265 | A1 | 4/2006 | Vaughan-Spickers et al. | |
| 2013/0090458 | A1 * | 4/2013 | Govindan et al. | 530/391.9 |

FOREIGN PATENT DOCUMENTS

| | | | |
|---|---|---|---|
| JP | 2002-509127 | | 3/2002 |
| JP | 2002-212121 | | 7/2002 |
| JP | 2008-524287 | | 7/2008 |
| WO | 0076551 | A2 | 12/2000 |
| WO | 0124763 | A2 | 4/2001 |
| WO | WO 2004054622 | A1 * | 7/2004 |
| WO | WO2007038658 | A2 | 4/2007 |

OTHER PUBLICATIONS

Walker et al. (Bioorganic and Medicinal Chemistry Letters 2002; 12: 217-219).*

Suzuwa et al. (J. Controlled Release 2002; 79: 229-242.*

Suzawa et al. (Bioorganic & Medicinal Chemistry 2000; 8: 2175-2184.*

Burkard et al. (Biochim Biophys Acta. Dec. 2010; 1806(2): 251-257).*

Gura (Science, 1997, 278:1041-1042).*

Kaiser (Science, 2006, 313: 1370).*

Krontiris and Capizzi (Internal Medicine, 4th Edition, Editor-in-chief Jay Stein, Elsevier Science, 1994 Chapters 71-72, pp. 699-729).*

Carter, S. K. et al. (Chemotherapy of Cancer; Second edition; John Wiley & Sons: New York, 1981; appendix C).*

Miller et al. (224th ACS National Meeting, Aug. 18-22, 2002, Boston, Mass., Poster Presentation, of record).

Voegelein et al. (J. Med. Chem. 1991; 34: 992-998).

Bennouna et al. (Int. J. Clin. Oncol. 2002; 7: 236-244).

Perez et al. (European Journal of Pharmacology 1998; 356: 239-243.

Trail, P. A., et al., "Carcinoma Reactive Doxorubicin (DOX) Conjugates: Comparison of BR64-DOX Conjugates Prepared with Disulfide or Thioether Linkers," Proceedings of the American Association for cancer Reserach, vol. 34, Mar. 1993, #2858, p. 479.

Shih, Lisa B., et al., "The Processing and Fate of Antibodies and Their Radiolabels Bound to the Surface of Tumor Cells in Vitro: A Comparison of Nine Radiolabels" J Nucl Med 1994; 35:899-908.

Kreitman, Robert J., et al., "*Pseudomonas* Exotoxin-based Immunotoxins Containing the Antibody LL2 or LL2-Fab' Indusc Regression of Subcutaneous Human B-Cell Lymphoma in Mice" Cancer Research 53, 819-825, Feb. 15, 1993.

(Continued)

*Primary Examiner* — Mark Halvorson
*Assistant Examiner* — Yan Xiao
(74) *Attorney, Agent, or Firm* — Richard A. Nakashima

(57) ABSTRACT

The invention relates to therapeutic conjugates with improved ability to target various diseased cells containing a targeting moiety (such as an antibody or antibody fragment), a linker and a camptothecin as a therapeutic moiety, and further relates to processes for making and using the said conjugates.

31 Claims, No Drawings

(56) References Cited

OTHER PUBLICATIONS

Guillemard, Veronique, et al., "Taxane-Antibody conjugates Afford Potent Cytotoxicity, Enhanced Solubility, and Tumor Target Selectivity" Cancer Research 61, 694-699, Jan. 15, 2001.
King, H. Dalton, et al., "Monoclonal Antibody Conjugates of Doxorubicin Prepared with Branched Linkers: A Novel Method for Increasing the Potency of Doxorubicin Immunoconjugates" Bioconjugate Chem. 1999, 10, 279-288, XP-000804254.
Chari, Ravi V., "Immunoconjugates containing Novel Maytansinoids: Promising Anticancer Drugs" 6175 Cancer Research 52(1992) Jan. 1, No. 1, Baltimore, MD, US XP000453560.
Heindel, Ned D., et al., "A Novel Heterobifunctional Linker for Formyl to Thiol Coupling" Bioconjugate Chem. 1991, 2, 427-430 XP-000983437.
Rowlinson-Busza, Gail, Msc., et al., "Targeted delivery of biologic and other antineoplaxtic agents" Current Opinion in Oncology 1992, 4:1142-1148 XP009027478.
Newton, et al. (Blood 2001; 97: 528-535.
Cao et al. (Bioconjugate Chemistry 1998; 9: 635-643).
Huan, Huey-Chung, et al., "The Rana Catesbeiana rer Gene Encoding a Cytotoxic Ribonuclease" The Journal of Biological Chemistry, vol. 273, No. 11, Issue of Mar. 13, pp. 6395-6401, 1998.
Fan et al., "Recoverable catalysts for asymmetric organic synthesis", Chem Rev. Oct. 2002;102(10):3385-466.
Govindan et al., "Advances in the use of monoclonal antibodies in cancer radiotherapy", Pharm Sci Technolo Today. Mar. 2000;3(3):90-98.
Moon et al., "Antibody conjugates of 7-ethyl-10-hydroxycamptothecin (SN-38) for targeted cancer chemotherapy", J Med Chem. Nov. 13, 2008;51(21):6916-26.

* cited by examiner

CAMPTOTHECIN-BINDING MOIETY CONJUGATES

RELATED APPLICATIONS

This application is a continuation-in-part of U.S. patent application Ser. No. 10/734,589, filed Dec. 15, 2003, which claimed the benefit under 35 USC 119(e) of provisional U.S. patent application Ser. No. 60/433,017, filed Dec. 13, 2002. The instant application claims the benefit under 35 USC 119(e) of provisional U.S. patent application Ser. Nos. 60/668,603, filed Apr. 6, 2005; 60/728,292, filed Oct. 20, 2005 and 60/751,196, filed Dec. 16, 2005. The text of each of the priority applications is incorporated herein by reference in its entirety.

FIELD OF THE INVENTION

The present invention relates to therapeutic conjugates with improved ability to target various cancer cells, infectious disease organisms and/or for treating autoimmune diseases, which conjugates contain a targeting (binding) moiety and a therapeutic moiety belonging to the camptothecin group of drugs. The targeting and therapeutic moieties are linked via an intracellularly cleavable linkage that increases therapeutic efficacy.

BACKGROUND OF THE INVENTION

For many years it has been an aim of scientists in the field of specifically targeted drug therapy to use monoclonal antibodies (MAbs) for the specific delivery of toxic agents to human cancers. Conjugates of tumor-associated MAbs and suitable toxic agents have been developed, but have had mixed success in the therapy of cancer, and virtually no application in other diseases. The toxic agent is most commonly a chemotherapy drug, although particle-emitting radionuclides, or bacterial or plant toxins have also been conjugated to MAbs.

The advantages of using MAb-chemotherapy drug conjugates are that (a) the chemotherapy drug itself is structurally well defined; (b) the chemotherapy drug is linked to the MAb protein using very well defined conjugation chemistries, often at specific sites remote from the MAbs antigen binding regions; (c) MAb-chemotherapy drug conjugates can be made more reproducibly than chemical conjugates involving MAbs and bacterial or plant toxins, and as such are more amenable to commercial development and regulatory approval; and (d) the MAb-chemotherapy drug conjugates are orders of magnitude less toxic systemically than radionuclide MAb conjugates.

The present disclosure solves specific problems associated with the preparation of conjugates of the camptothecin (CPT) group of cytotoxic compounds. CPT and its derivatives are a class of potent antitumor agents. Irinotecan (also referred to as CPT-11) and topotecan are CPT analogs that are approved cancer therapeutics (Iyer and Ratain, *Cancer Chemother. Phamacol.* 42: S31-S43 (1998)). CPTs act by inhibiting topoisomerase I enzyme by stabilizing topoisomerase I-DNA complex (Liu, et al. in *The Camptothecins: Unfolding Their Anticancer Potential*, Liehr J. G., Giovanella, B. C. and Verschraegen (eds), NY Acad. Sci., NY 922:1-10 (2000)).

CPTs present a set of caveats in the preparation of conjugates. One caveat is the insolubility of most CPT derivatives in aqueous buffers. Secondly, CPTs provide specific challenges for structural modification for conjugating to macromolecules. For instance, CPT itself contains only a tertiary hydroxyl group in ring-E. The hydroxyl functional group in the case of CPT must be coupled to a linker suitable for subsequent protein conjugation; and in potent CPT derivatives, such as SN-38, the active metabolite of the chemotherapeutic CPT-11, and other C-10-hydroxyl-containing derivatives such as topotecan and 10-hydroxy-CPT, the presence of phenolic hydroxyl at C-10 position complicates the necessary C-20-hydroxyl derivatization. Thirdly the lability of the δ-lactone moiety of the E-ring of their structures, under physiological conditions, results in greatly reduced antitumor potency of these products. Therefore, the conjugation protocol is performed such that it is carried out at a pH of 7 or lower to avoid the lactone ring opening. Typically conjugation of a bifunctional CPT possessing an amine-reactive group such as an active ester would require a pH of 8 or greater. Fourth, an intracellularly-cleavable moiety is to be incorporated in the linker/spacer connecting the CPTs and the antibodies or other binding moieties.

The problem of 6-lactone opening under physiological conditions has been previously addressed. One approach has been to acylate the C-20 hydroxyl group with an amino acid, and couple the α-amino group of the amino acid to poly-L-glutamic acid (Singer et al. in *The Camptothecins: Unfolding Their Anticancer Potential*, Liehr J. G., Giovanella, B. C. and Verschraegen (eds), NY Acad. Sci., NY 922 :136-150 (2000)). This approach relies on the passive diffusion of a polymeric molecule into tumor sites. This glycine conjugation has also been reported as a method of making water-soluble derivative of CPT (Vishnuvajjala et al., U.S. Pat. No. 4,943,579) and in the preparation of a PEG-derivatization of CPT (Greenwald, et al. *J. Med. Chem.* 39: 1938-1940 (1996). In the latter case, the approach has been devised in the context of developing water-soluble and long acting forms of CPT, whereby CPT's in vivo half-life is enhanced, and the drug is gradually released from its conjugate while in circulation in vivo.

The present invention discloses methods for preparing conjugates of CPTs, of 10-hydroxy derivatives such as SN-38 in particular, taking into consideration the four caveats described above and the synthetic challenges. SN-38 is the active drug form of the approved cancer drug CPT-11, which is a prodrug. Vast clinical data are available concerning CPT-11 pharmacology and of its in vivo conversion to SN-38 (Iyer and Ratain, supra; Mathijssen et al., *Clin Cancer Res.* 7:2182-2194 (2002); Rivory, *Ann NY Acad. Sci.* 922:205-215, 2000)). The active form SN-38 is about 2 to 3 orders of magnitude more potent than CPT-11.

Early work on protein-drug conjugates indicated that a drug ideally needed to be released in its original form, once it had been internalized into a target cell, for the protein-chemotherapy drug conjugate to be a useful therapeutic. Trouet et al. (*Proc. Natl. Acad. Sci. USA* 79:626-629 (1982)) showed the advantage of using specific peptide linkers, between the drug and the targeting moiety, which are cleaved lysosomally to liberate the intact drug. Work during the 1980's and early 1990's focused further on the nature of the chemical linker between the chemotherapeutic drug and the MAb. Notably, MAb-chemotherapy drug conjugates prepared using mild acid-cleavable linkers were developed, based on the observation that the pH inside tumors was often lower than normal physiological pH. In this respect, superior results were found by incorporating a hydrazone as a cleavable unit, and attaching DOX to a MAb via a thioether group, (Willner et al., U.S. Pat. No. 5,708,146; Trail et al. (*Science* 261:212-215 (1993)). This approach showed that MAb-doxorubicin (DOX) conjugates, prepared with appropriate linkers, could be used to cure mice bearing a variety of human tumor xenografts, in preclinical studies. The first approved MAb-drug conjugate, Gemtuzumab Ozogamicin, incorporates a similar acid-labile hydrazone bond between an anti-CD33 antibody, humanized P67.6, and a potent calicheamicin derivative. Sievers et al., *J Clin Oncol.* 19:3244-3254 (2001); Hamann et al., *Bioconjugate Chem.* 13: 47-58 (2002). In some cases, the MAb-chemotherapy drug conjugates were made with reductively labile hindered disulfide bonds between the chemotherapy drugs and the MAb (Liu et al., *Proc Natl Acad Sci USA* 93: 8618-8623 (1996)). Yet another cleavable linker involves a cathepsin B-labile dipeptide spacers, such as Phe-Lys or Val-Cit, similar to the lysosomally labile peptide spacers of Trouet et al. containing from one to four amino acids, which additionally incorporated a collapsible spacer between the drug and the dipeptide (Dubowchik, et al., *Bioconjugate Chem.* 13:855-869 (2002); Firestone et al., U.S. Pat. No. 6,214,345 B1; Doronina et al., *Nat Biotechnol.* 21: 778-784 (2003)). The latter approaches were also utilized in the preparation of an immunoconjugate of camptothecin (Walker et al., *Bioorg Med Chem Lett.* 12:217-219 (2002)). Another cleavable moiety that has been explored is an ester linkage incorporated into the linker between the antibody and the chemotherapy drug. Gillimard and Saragovi have found that when an ester of paclitaxel was conjugated to anti-rat p75 MAb, MC192, or anti-human TrkA MAb, 5C3, the conjugate was found to exhibit target-specific toxicity. Gillimard and Saragovi, *Cancer Res.* 61:694-699 (2001).

While the importance of cleavable linker in the design of binding moiety-drug conjugates cannot be overstated, it is also important to focus on how the linker design impacts the overall preparation of specific CPT-binding moiety conjugates. The present invention solves the problem associated with the preparation of the bifunctional drug-linker molecule, wherein the said drug may also contain more than one reactive group for derivatization, such as the potent SN-38 analog, for instance, in the design of conjugates. SN-38, a clinically important active drug form of the cancer drug CPT-11, but 100-1000-times more potent than CPT-11, is not useable systemically because of insolubility. The present invention solves this problem by conjugating it to a targeting moiety in ways that also address other challenges of using a CPT, while concurrently improving the therapeutic index of this clinically important potent drug by using disease-specific antibodies.

The conjugates of the instant invention possess greater efficacy, in many cases, than unconjugated or "naked" antibodies or antibody fragments, although such unconjugated targeting molecules have been of use in specific situations. In cancer, for example, naked antibodies have come to play a role in the treatment of lymphomas (Campath® and Rituxan®), colorectal and other cancers (Erbitux® and Avastin®), breast cancer (Hereceptin®), as well as a large number now in clinical development (e.g., epratuzumab). In most of these cases, clinical use has involved combining these naked, or unconjugated, antibodies with other therapies, such as chemotherapy or radiation therapy. A variety of antibodies are also in use for the treatment of autoimmune and other immune dysregulatory diseases, such as tumor necrosis factor (TNF) and B-cell (Rituxan®) antibodies in arthritis, and are being investigated in other such diseases, such as the B-cell antibodies Rituxan® and epratuzumab in systemic lupus erythematosus and Sjögren's syndrome, as well as juvenile diabetes and multiple sclerosis. Naked antibodies are also being studied in sepsis and septic shock, Alzheimer's disease, and infectious diseases. The development of anti-infective monoclonal antibodies has been reviewed recently by Reichert and Dewitz (Nat Rev Drug Discovery 2006; 5:191-195), incorporated herein by reference, which summarizes the priority pathogens against which naked antibody therapy has been pursued, resulting in only 2 pathogens against which antibodies are either in Phase III clinical trials or are being marketed (respiratory syncytial virus and methicillin-resistant *Staphylococcus aureus*), with 25 others in clinical studies and 20 discontinued during clinical study. Thus, there is a need to develop more potent anti-pathogenic antibodies and other binding moieties.

SUMMARY OF THE INVENTION

The present invention resolves an unfulfilled need in the art by providing improved methods and compositions for preparation of camptothecin-binding moiety conjugates. The disclosed methods and compositions are of use for the treatment of a variety of diseases and conditions which are refractory or less responsive to other forms of therapy, and can include diseases against which suitable targeting moieties for selective targeting can be developed, or are available or known. Preferably, this targeting moiety is an antibody, antibody fragment, bispecific or other multivalent antibody, or other antibody-based molecule or compound. However, other binding moieties known in the art, such as aptamers, avimers or targeting peptides, may be used. Preferred diseases or conditions against which such targeting moieties exist are, for example, cancer, immune dysregulatory conditions, including autoimmune diseases and inflammatory diseases, diseases caused by infectious organisms, neurodegenerative diseases (e.g., Alzheimer's diseases), and cardiovascular diseases (fibrin clots, atherosclerosis, myocardial iscehmia and infarcts).

The disclosed methods and compositions may thus be applied for treatment of diseases and conditions for which targeting moieties are of use to deliver camptothecin-related cytotoxic agents. Such diseases or conditions may be characterized by the presence of a target molecule or target cell that is insufficiently affected when unconjugated, or naked, targeting moieties are used, such as in the immunotherapy of cancer or of infection with pathogenic organisms. (For methods of making immunoconjugates of antibodies with isotopes, drugs, and toxins for use in disease therapies, see, e.g., U.S. Pat. Nos. 4,699,784; 4,824,659; 5,525,338; 5,677,427; 5,697,902; 5,716,595; 6,071,490; 6,187,284; 6,306,393; 6,653,104; 6,962,702; and U.S. Patent Appln. Publ. Nos. 20050191239; 20050175582; 20050136001; 20040166115; 20040043030; 20040022725; 20030068322; 20030031669; 20030026764 and 20020136690, each incorporated in their entirety by reference.)

In certain exemplary embodiments, camptothecin conjugates of antibodies or antibody fragments may be used for targeting this therapeutic drug to pathogens, such as bacteria, viruses, fungi, and parasites. In preferred embodiments, such drug-conjugated targeting moieties can be used in combination with other therapeutic modalities, such as anti-fungal, antibiotics and antiviral drugs and/or naked antibodies, immunomodulators (e.g., interferon and/or cytokines). The use of radioimmunotherapy for the treatment of infectious organisms is disclosed, for example, in U.S. Pat. Nos. 4,925,648; 5,332,567; 5,439,665; 5,601,825; 5,609,846; 5,612,016; 6,120,768; 6,319,500; 6,458,933; 6,548,275; and in U.S. Patent Application Publication Nos. 20020136690 and 20030103982, each of which are incorporated herein by reference in their entirety.

In certain embodiments involving treatment of cancer, the camptothecin conjugates may be used in combination with surgery, radiation, chemotherapy, immunotherapy with naked antibodies, radioimmunotherapy, immunomodulators, and the like. Similar combinations are preferred in the treatment of the other diseases amenable to targeting moieties, such as cardiovascular, autoimmune, and neurodegenerative diseases. For example, the camptothecin conjugates can be combined with TNF inhibitors, B-cell antibodies, and other effective agents for the treatment of autoimmune diseases, such as rheumatoid arthritis, systemic lupus erythematosis, Sjögren's syndrome, multiple sclerosis, vasculitis, as well as type-I diabetes (juvenile diabetes). These combination therapies can allow lower doses of each therapeutic to be given in such combinations, thus reducing certain severe side effects, and potentially reducing the courses of therapy required.

In one embodiment, the invention relates to a conjugate comprising:

(a) a targeting moiety;

(b) a therapeutic moiety which is camptothecin (CPT) or its derivative or analog; and (c) a linker binding to the targeting moiety via targeting moiety-coupling functional group, and to the CPT moiety via an intracellularly-cleavable moiety.

In another embodiment, the invention relates to a conjugate comprising:

(a) a targeting moiety;

(b) a therapeutic moiety which is camptothecin (CPT) or its derivative or analog; and (c) a linker binding to the targeting moiety via targeting moiety-coupling functional group, and to the CPT or its derivative via C-terminus of an amino acid attached to the intracellularly-cleavable moiety.

In a further embodiment, the invention relates to a process of preparing conjugates, wherein the linker is first conjugated to a CPT drug, thereby producing a CPT drug-linker conjugate; wherein said CPT drug-linker conjugate preparation involves the selective protection and deprotection of C-10 hydroxyl group, keeping the C-20 carbonate bond essentially intact, in derivatives of CPT containing a C-10 hydroxyl group; wherein said drug-linker conjugate is optionally not purified; and wherein said drug-linker conjugate is subsequently conjugated to a monoclonal antibody or fragment.

Yet another embodiment of the invention is a method of treating cancer, a malignancy, an autoimmune disease, an infection, or an infectious lesion with the conjugates described herein.

DEFINITIONS

Unless otherwise specified, "a" or "an" means "one or more."

In the description that follows, a number of terms are used and the following definitions are provided to facilitate understanding of the present invention. Terms that are not expressly defined herein are used in accordance with their plain and ordinary meanings.

The term targeting moiety as used herein refers to a molecule, complex or aggregate, that binds specifically or selectively to a target molecule, cell, particle, tissue or aggregate. In preferred embodiments, a targeting moiety is an antibody, antibody fragment, bispecific antibody or other antibody-based molecule or compound. However, other examples of targeting moieties are known in the art and may be used, such as aptamers, avimers, receptor-binding ligands, nucleic acids, biotin-avidin binding pairs, binding peptides or proteins, etc. The terms "targeting moiety" and "binding moiety" are used synonymously herein.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. An antibody or antibody fragment may be conjugated or otherwise derivatized within the scope of the claimed subject matter.

An antibody fragment is a portion of an antibody such as $F(ab')_2$, $F(ab)_2$, Fab', Fab, Fv, scFv (single chain Fv) and the like. Regardless of structure, an antibody fragment of use binds with the same antigen that is recognized by the intact antibody. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region, such as CDRs. The Fv fragments may be constructed in different ways to yield multivalent and/or multispecific binding forms. In the former case of multivalent, they react with more than one binding site against the specific epitope, whereas with multispecific forms, more than one epitope (either of the antigen or even against the specific antigen and a different antigen) is bound. As used herein, the term antibody component includes both an entire antibody, a fusion protein, and fragments thereof.

A naked antibody is generally an entire antibody that is not conjugated to a therapeutic agent. This is so because the Fc portion of the antibody molecule provides effector or immunological functions, such as complement fixation and ADCC (antibody dependent cell cytotoxicity), which set mechanisms into action that may result in cell lysis. However, the Fc portion may not be required for therapeutic function of the antibody, but rather other mechanisms, such as apoptosis, anti-angiogenesis, anti-metastatic activity, anti-adhesion activity, such as inhibition of heterotypic or homotypic adhesion, and interference in signaling pathways, may come into play and interfere with the disease progression. Naked antibodies include both polyclonal and monoclonal antibodies, and fragments thereof, that include murine antibodies, as well as certain recombinant antibodies, such as chimeric, humanized or human antibodies and fragments thereof. Therefore, in some cases a "naked antibody" may also refer to a "naked" antibody fragment. As defined in the present invention, "naked" is synonymous with "unconjugated," and means not linked or conjugated to the therapeutic agent with which it administered.

Autoimmune Diseases are disorders that are caused by the body producing an immune response against its own tissues. Examples include Class III autoimmune diseases such as immune-mediated thrombocytopenias, such as acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, rheumatoid arthritis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis, as disclosed in U.S. Provisional Application Ser. No. 60/360,259, filed Mar. 1, 2002, incorporated herein by reference.

A chimeric antibody is a recombinant protein that contains the variable domains of both the heavy and light antibody chains, including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, is transferred from the heavy and light variable chains of the rodent antibody into human heavy and light variable domains. The constant domains of the antibody molecule are derived from those of a human antibody. In some cases, specific residues of the framework region of the humanized antibody, particularly those that are touching or close to the CDR sequences, may be modified, for example replaced with the corresponding residues from the original rodent or other antibody.

A human antibody is an antibody obtained, for example, from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, which are incorporated in their entirety by reference.

Infectious Diseases as used herein are diseases involving infection by pathogens such as bacteria, *rickettsia*, mycoplasma, protozoa, fungi, viruses, parasites, or other microbial agents. Examples include human immunodeficiency virus (HIV) causing AIDS, *Mycobacterium* of tuberculosis, *Streptococcus agalactiae*, methicillin-resistant *Staphylococcus aureus, Legionella pneumophilia, Streptococcus pyogenes, Escherichia coli, Neisseria gonorrhosae, Neisseria meningitidis, Pneumococcus, Hemophilis influenzae B, Treponema pallidum*, Lyme disease spirochetes, West Nile virus, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reo virus, polio virus, simian virus 40, mouse mammary tumor virus, dengue virus, rubella virus, *Plasmodium falciparum, Plasmodium vivax, Toxoplasma gondii, Trypanosoma rangelii, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae.*

A therapeutic agent is a molecule or atom that is administered separately, concurrently or sequentially with a binding moiety, e.g., an antibody or antibody fragment, or a subfragment thereof, and is useful in the treatment of a disease. Examples of therapeutic agents include, but are not limited to, antibodies, antibody fragments, conjugates, drugs, cytotoxic agents, toxins, nucleases, hormones, immunomodulators, chelators, boron compounds, photoactive agents or dyes, radioisotopes or radionuclides, oligonucleotides, interference RNA, peptides, antiangiogenic agents, chemotherapeutic agents, cyokines, chemikines, drugs, prodrugs, toxins, enzymes, binding proteins or peptides, conjugates or combinations thereof.

A conjugate is an antibody component or other targeting moiety conjugated to a therapeutic agent. Suitable therapeutic agents are described above.

As used herein, the term antibody fusion protein is a recombinantly-produced antigen-binding molecule in which two or more of the same or different natural antibody, single-chain antibody or antibody fragment segments with the same or different specificities are linked. A fusion protein comprises at least one specific binding site. Valency of the fusion protein indicates the total number of binding arms or sites the fusion protein has to antigen(s) or epitope(s); i.e., monovalent, bivalent, trivalent or mutlivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG, is bivalent because it has two binding arms but is monospecific because it binds to one type of antigen or epitope. A monospecific, multivalent fusion protein has more than one binding site for the same antigen or epitope. For example, a monospecific diabody is a fusion protein with two binding sites reactive with the same antigen. The fusion protein may comprise a multivalent or multispecific combination of different antibody components or multiple copies of the same antibody component. The fusion protein may additionally comprise a therapeutic agent.

An immunomodulator is a therapeutic agent that when present, alters, suppresses or stimulates the body's immune system. Typically, an immunomodulator of use stimulates immune cells to proliferate or become activated in an immune response cascade, such as macrophages, B-cells, and/or T-cells. However, in some cases an immunomodulator of use, may suppress proliferation or activation of immune cells, as in therapeutic treatment of autoimmune disease. An example of an immunomodulator as described herein is a cytokine, which is a soluble small protein of approximately 5-20 kDs that are released by one cell population (e.g., primed T-lymphocytes) on contact with specific antigens, and which act as intercellular mediators between cells. As the skilled artisan will understand, examples of cytokines include lymphokines, monokines, interleukins, and several related signaling molecules, such as tumor necrosis factor (TNF) and interferons. Chemokines are a subset of cytokines. Certain interleukins and interferons are examples of cytokines that stimulate T cell or other immune cell proliferation.

CPT is abbreviation for camptothecin, and in this application CPT represents camptothecin itself or an analog or derivative of camptothecin. The structures of camptothecin and some of its analogs, with the numbering indicated and the rings labeled with letters A-E, are given in formula 1 in Chart 1 below.

Chart 1

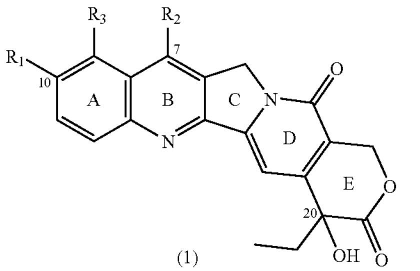

(1)

CPT: $R_1 = R_2 = R_3 = H$

10-Hydroxy-CPT: $R_1 = OH$; $R_2 = R_3 = H$

CPT-11: $R_1$ =

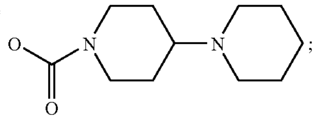

$R_2$ = ethyl; $R_3$ = H

SN-38: $R_1$ = OH; $R_2$ = ethyl; $R_3$ = H

Topotecan: $R_1$ = OH; $R_2$ = H; $R_3$ = $CH_2$—$N(CH_3)_2$

DETAILED DESCRIPTION OF THE INVENTION

Methods are devised in the following ways for the preparation of conjugates of CPT or a CPT analog or derivative (collectively 'CPT') with targeting moiety such as an antibody (MAb). The disclosed methods represent a preferred embodiment of the invention. (1) Solubility of CPT is enhanced by placing a polyethyleneglycol moiety (PEG) between CPT and the antibody; (2) a lysosomally cleavable linker such as a peptide spacer is placed between CPT and antibody for the intracellular liberation of intact CPT; (3) the lysosomally cleavable peptide spacer is attached through a collapsible linker to CPT in the form of a carbonate, or in the form of a carbamate via an ester at CPT's C-20 position; (4) the antibody-coupling group is designed to be either a thiol or a thiol-reactive group; and (5) methods are devised for selective regeneration of the 10-hydroxyl group in presence of the C-20 carbonate in preparations of drug-linker precursor involving CPT analogs such as SN-38. In the following discussion, where a conjugate comprises an antibody or antibody fragment, another type of binding moiety, such as an aptamer, avimer or targeting peptide, may be substituted.

Method 1

An exemplary preferred embodiment is directed to a conjugate of a camptothecin drug derivative and an antibody of the general formula 2, MAb-[L]-AA-CPT (2)

where MAb is a disease-targeting antibody; CPT is camptothecin (CPT) or an analog thereof; and L is the linker system of the type X-Y-Z wherein X is an antibody-coupling moiety, Y is a lysosomally cleavable polypeptide, and Z is 4-aminobenzyloxy moiety, which is connected to the CPT drug. X and Y may be linked via an amide bond, with an intervening spacer which is a straightchain or cyclic hydrocarbon, or which is a water-solubilizing moiety such as polyethyleneglycol (PEG). AA is an amino acid or polypeptide moiety forming an ester between and the 20-hydroxyl of CPT, and further attached via its (AA's) N-terminus to the 'Z' component of linker 'L'.

In a preferred embodiment of Method 1, the intracellularly-cleavable moiety is optionally cleavable by intracellular esterases. In a preferred embodiment, the intracellularly-cleavable moiety is an ester moiety formed between the carboxylic acid of an amino acid such as glycine, alanine, or sarcosine, or of a peptide such as glycylglycine, and the 20-hydroxyl of CPT. In these cases, the N-terminus of the said amino acid or polypeptide is protected as a Boc or a Fmoc or a monomethoxytrityl (MMT) derivative, which is deprotected after formation of an ester bond with 20-hydroxyl of CPT. Selective removal of amine-protecting group, in presence of a BOC protecting group at the C-10-hydroxyl position of CPT analogs containing the additional 10-hydroxyl group, as in some analogs shown in Chart 1, is achieved using the MMT as the protecting group for the amino group of amino acid or polypeptide involved in ester formation, since 'MMT' is removable by mild acid treatment such as dichloroacetic acid that does not cleave a BOC group.

In a preferred embodiment of Method 1, intracellularly-cleavable moiety further comprises a polypeptide as an embodiment of the 'Y' component of linker 'L' that is cleavable by intracellular enzymes such as Cathepsin B. The latter product is generated by coupling CPT-derived ester to 'Z' of the linker 'L' shown above, through the activated form of p-aminobenzyl alcohol, namely PABOCOPNP where PNP is p-nitrophenyl. In a preferred embodiment, the linker comprises a thiol-reactive group which links to thiol groups of said targeting moiety. The thiol-reactive group is optionally a maleimide or vinylsulfone, or bromoacetamide, or iodoacetamide, which links to thiol groups of said targeting moiety. In a preferred embodiment, said reagent bearing a thiol-reactive group is generated from succinimidyl-4-(N maleimidomethyl)cyclohexane-1-carboxylate (SMCC) or from succinimidyl-ϵ-maleimido)caproate, for instance, with the thiol-reactive group being a maleimide group.

In a preferred embodiment of Method 1, the conjugate contains polyethyleneglycol (PEG) spacer between X and Y of the general formula; PEG can be of up to MW 5000 in size, and in a preferred embodiment, PEG is a defined PEG with (1-12 or 1-36) repeating monomeric units, and in a more preferred embodiment, PEG is a defined PEG with 1-12 repeating monomeric units. The introduction of PEG may involve using heterobifunctionalized PEG derivatives which are available commercially. In the context of the present invention, the heterobifunctional PEG contains an antibody or binding moiety-coupling group such as, for example, a maleimide moiety or a protected thiol moiety as well as an activated ester such as succinimidyl carboxylate. An example of a heterobifunctional defined PEG containing 12 repeating monomeric units, with 'NHS' being succinimidyl, is given below in formula 3:

(3)

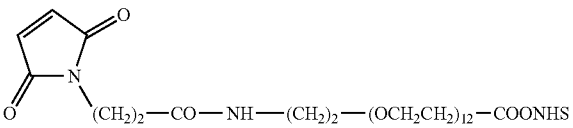

A representative SN-38 (a CPT analog containing additional hydroxyl group) conjugate of an antibody, prepared with a maleimide-containing SN-38-linker derivative, with the bonding to MAb represented as a succinimide, is given below. Here, the 20-O-AA ester bonding to SN-38 is sarcosinate.

(4)

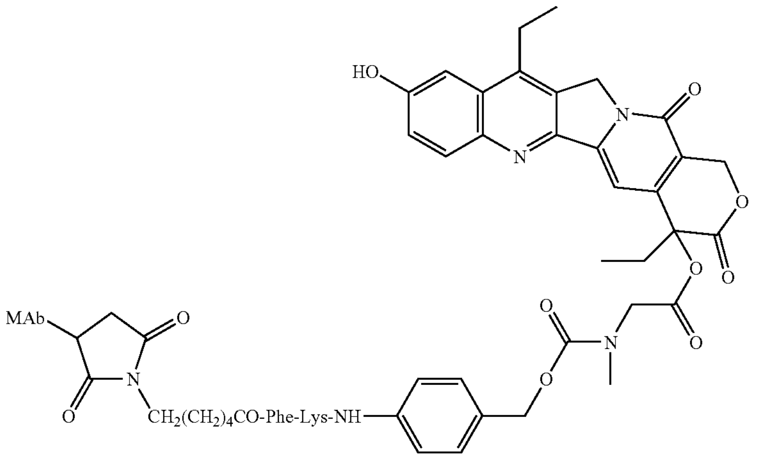

A representative CPT conjugate of an antibody of Method 1, prepared with a maleimide-PEG-containing SN-38-linker derivative, with the bonding to MAb represented as a succinimide, is given below. Here, the 20-O-AA ester bonding to SN-38 is glycinate.

(5)

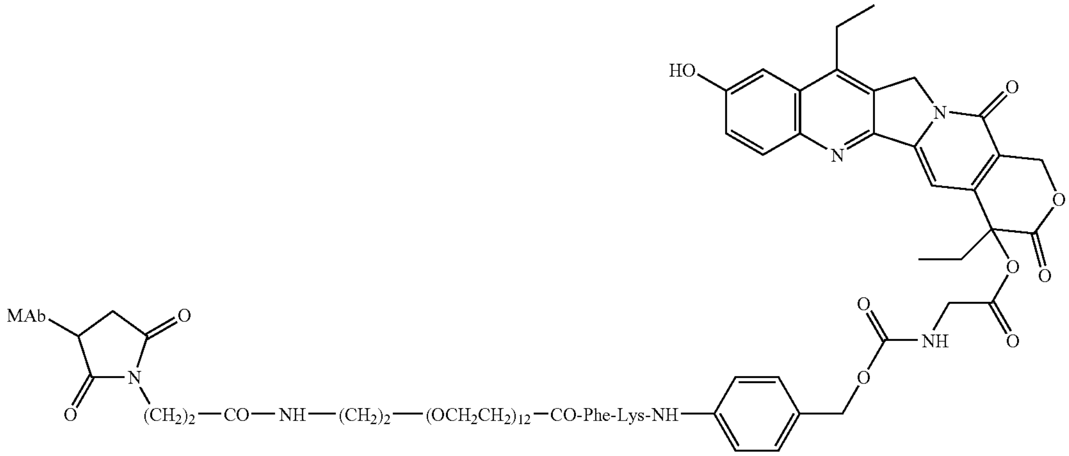

In Method 1, when the 'X' group is a thiol-reactive moiety, the thiols on the antibody are generated on the lysine groups of the antibody using a thiolating reagent. Methods for introducing thiol groups on to antibodies by modifications of MAb's lysine groups are well known in the art (Wong in *Chemistry of protein conjugation and cross-linking*, CRC Press, Inc., Boca Raton, Fla. (1991), pp 20-22). Alternatively, mild reduction of interchain disulfide bonds on the antibody (Willner et al., *Bioconjugate Chem.* 4:521-527 (1993)) using reducing agents such as dithiothreitol (DTT) can generate 7-to-10 thiols on the antibody; which has the advantage of incorporating multiple CPT moieties upon reaction with [L]-ester-CPT of the general formula given above, in the interchain region of MAb away from antigen-binding region. By this way, the CPT with a thiol-reactive group can be conjugated to MAb either site-specifically on the cysteines generated by disulfide reduction or indirectly on the lysine side chains of MAb derivatized to possess thiol groups.

Furthermore, in a preferred embodiment of Method 1, the linker comprises a thiol group that reacts with a thiol-reactive residue introduced at one or more lysine side chain amino groups of said targeting moiety. In Method 1, when the 'X' group is thiol, as in a case where the bond between X and Y is a thiopropionyl moiety, for example, the antibody is pre-derivatized with a thiol-reactive group such as a maleimide, vinylsulfone, bromoacetamide, or iodoacetamide by procedures well described in the art.

The cleavable peptide Y of Method 1 may be selected from the group consisting of Phe-Lys, Val-Cit (Dubowchik, supra), Ala-Leu, Leu-Ala-Leu, and Ala-Leu-Ala-Leu (Trouet et al., supra).

In a preferred embodiment of the present invention, the preferred chemotherapeutic moiety is selected from the group consisting of CPT, 10-hydroxy camptothecin, SN-38, topotecan, lurtotecan, 9-aminocamptothecin, 9-nitrocamptothecin, and derivatives thereof. In a more preferred embodiment, the chemotherapeutic moiety is SN-38. Preferably, in the conjugates of the preferred embodiments of the present invention, the targeting moiety links to at least one chemotherapeutic moiety; preferably 1 to about 12 chemotherapeutic moieties; most preferably about 7 to about 12 chemotherapeutic moieties.

Method-2

Another exemplary embodiment is directed to a conjugate of a camptothecin drug derivative and an antibody of the general formula 6:

MAb-[L]-CPT (6)

where MAb is a disease-targeting antibody; CPT is camptothecin (CPT) or an analog thereof; and L is the linker system of the type X-Y-Z wherein X is an antibody-coupling moiety, Y is a lysosomally cleavable polypeptide, and Z is 4-aminobenzyloxy moiety, which is directly or indirectly connected to the CPT drug; finally, X and Y are linked via an amide bond, with an intervening spacer which is a straight chain or cyclic hydrocarbon, or which is a water-solubilizing moiety such as polyethyleneglycol (PEG). In the embodiment of Method 2, the linker 'L' consisting of X-Y-Z is attached directly or indirectly to 20-O-carbonyl moiety of CPT.

All embodiments of the linker 'L' (X-Y-Z), stipulated for Method 1 in paragraphs 0038, 0040, 0041, and 0044-0047 apply to Method 2 embodiments in their entirety, except that the mode of attachment of 'Z' is either via PABOH moiety when reacted directly with the chloroformate of hydroxyl at C-20 position of CPT to form a carbonate, or via activated form of PABOH when reacted with the amine terminus of a carbamate at the C-20 position.

A representative CPT conjugate of an antibody of Method 2, prepared with a maleimide-containing SN-38-linker derivative, with the bonding to MAb represented as a succinimide, is given below:

(7)

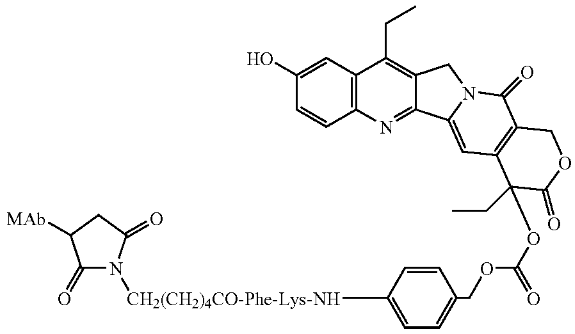

A representative CPT conjugate of an antibody of Method 2, prepared with a maleimide-PEG-containing SN-38-linker derivative, with the bonding to MAb represented as a succinimide, is given below:

(8)

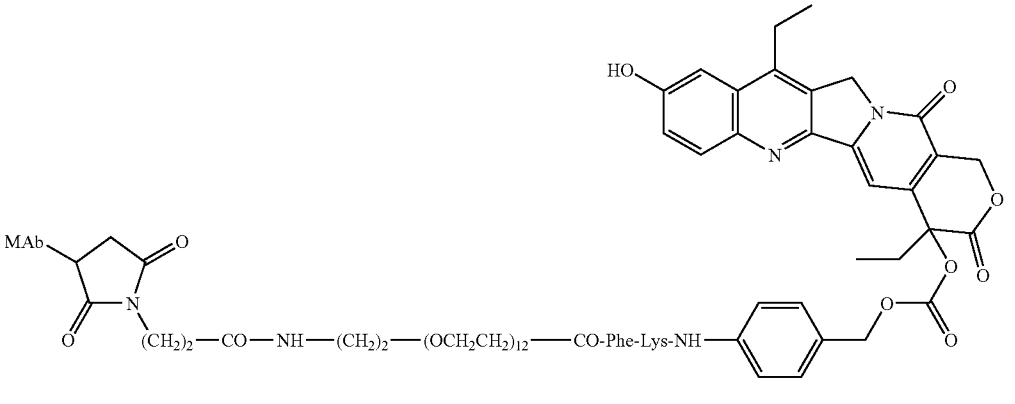

Another embodiment of Method 2 is shown by the structural formula 9. All embodiments of the linker 'L' (X-Y-Z), stipulated for Method 1 in paragraphs 0038, 0040, 0041, and 0044-0047 apply to this Method 2 embodiment in their entirety. Here, the activated form of 'Z', namely PAB-OCOPNP where PNP is p-nitrophenyl, is bonded to a 20-carbamate derivative of CPT, the latter derived from 20-chloroformate of a CPT and a N-monosubstituted, or N,N'-disubstituted, or unsubstituted, ethylenediamine. A representative CPT conjugate of an antibody of Method 2, prepared with a maleimide-containing SN-38-linker derivative, with bonding to MAb represented as a succinimide, is given below. Here, the N,N'-dimethylethylenediamine is used to link 'L' with 20-chloroformate of SN-38. While not wishing to be bound by theory, the terminal amino group of the drug-20-carbamate, generated after intracellular processing, can cyclize to a 5-membered ring to release free CPT (SN-38 in this case). Alternatively, the N,N'-dimethylethylenediamine spacer in the structure below can be substituted with sarcosine hydrazide, with sarcosine amino group reacted with a CPT (or analog such as SN-38)-20-chloroformate, and the hydrazide part coupled to the 'L' linker system. In this case, the hydrazide liberated after intracellular catabolism of the antibody and the linker can also cyclize to give a 6-membered ring, with the concomitant liberation of free CPT (or analog, such as SN-38) molecule. The ethylenediamine version as well as the hydrazide version enumerated herein are within the purview of the present invention.

(9)

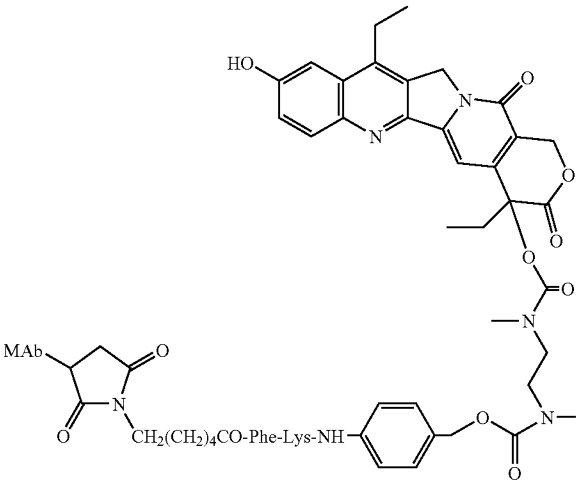

Furthermore, in a preferred embodiment of Method 2, the linker comprises a thiol group which reacts with a thiol-reactive residue at a lysine side chain of said targeting moiety, where said thiol-reactive moiety is selected from the group comprising maleimide, vinylsulfone, bromoacetamide, and iodoacetamide.

A representative CPT conjugate of an antibody of Method 2, prepared with a thiol-containing SN-38-linker derivative, with the bonding to MAb represented as a succinimide, is given below.

(10)

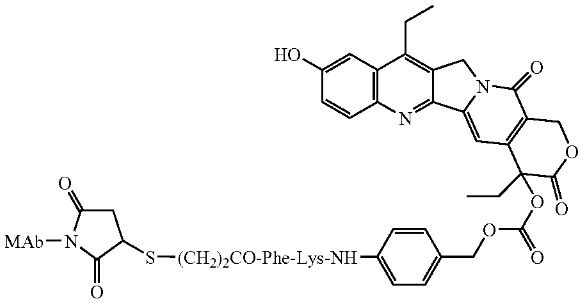

Method 3

Yet another exemplary embodiment is directed to a conjugate of a camptothecin drug derivative and an antibody of the general formula 11:

MAb-[cross-linker]-AA-CPT (11)

wherein CPT's 20-O-AA ester, formed with the C-terminus of an amino acid or polypeptide moiety 'AA', is directly coupled to the antibody-coupling group 'X', thereby eliminating the 'Y-Z' component of the linker 'L' of Schemes 1 & 2. All embodiments of 'X', together with the spacer aspect pertaining to the bonding between 'X' and 'Y', and CPT definitions of Methods 1 & 2 apply in their entirety herein, with the exception that in Method 3, the spacer between 'X' and 'Y' is replaced by the spacer between 'X' and the amine terminus of the ester.

A representative CPT conjugate of an antibody of Method 3, prepared with a maleimide-PEG-containing SN-38-linker derivative, with the bonding to MAb represented as a succinimide, is given below.

(12)

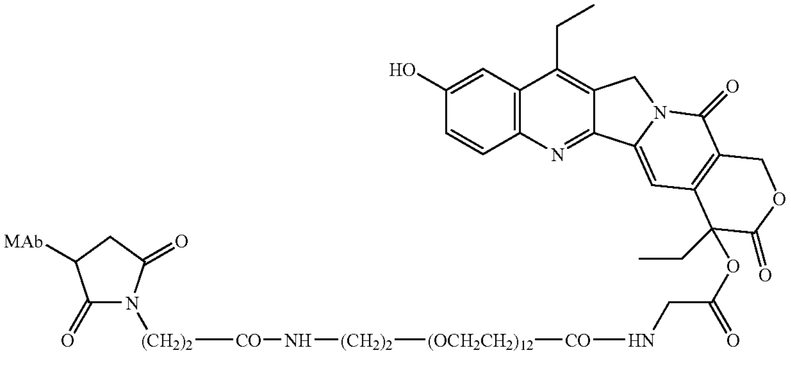

Other embodiments are additionally directed to a process for producing said MAb-CPT conjugates whereby the linker 'L' of Methods 1-3 is first conjugated to a derivatized form of a CPT drug, and this process is followed by removing protecting groups on some functional groups on the linker as well as that which may be present on CPT, wherby a CPT drug-linker conjugate is obtained. The CPT drug-linker conjugate is subsequently conjugated to a MAb or fragment.

In the context of embodiments in 0048-0054, a process was surprisingly discovered by which CPT drug-linkers can be prepared wherein CPT additionally has a 10-hydroxyl group. This process involves, but is not limited to, the protection of the said 10-hydroxyl group as a t-butyloxycarbonyl (BOC) derivative, followed by the preparation of the penultimate intermediate of the drug-linker conjugate. Usually, removal of BOC group requires treatment with strong acid such as trifluoroacetic acid (TFA). Under these conditions, the CPT 20-O-linker carbonate, containing protecting groups to be removed, is also susceptible to cleavage, thereby giving rise to unmodified CPT. In fact, the rationale for using a mildly removable methoxytrityl (MMT) protecting group for the lysine side chain of the linker molecule, as enunciated in the art, was precisely to avoid this possibility (Walker et al., supra). It was discovered that selective removal of phenolic BOC protecting group is possible by carrying out reactions for short durations, optimally 3-to-5 minutes. Under these conditions, the predominant product was that in which the 'BOC' at 10-hydroxyl position was removed, while the carbonate at '20' position was intact.

In one embodiment, the targeting moiety is a monoclonal antibody (MAb). In a further embodiment, the targeting moiety may be a multivalent and/or multispecific MAb. The targeting moiety may be a murine, chimeric, humanized, or human monoclonal antibody, and said antibody is in intact, fragment (Fab, Fab', $F(ab)_2$, $F(ab')_2$), or sub-fragment (single-chain constructs) form.

In a preferred embodiment, the targeting moiety is a monoclonal antibody that is reactive with an antigen or epitope of an antigen expressed on a cancer or malignant cell. The cancer cell is preferably a cell from a hematopoietic tumor, carcinoma, sarcoma, melanoma or a glial tumor.

A preferred malignancy to be treated according to the present invention is a malignant solid tumor or hematopoietic neoplasm.

In a preferred embodiment, the intracellularly-cleavable moiety may be cleaved after it is internalized into the cell upon binding by the MAb-drug conjugate to a receptor thereof, and particularly cleaved by esterases and peptidases.

The targeting moiety is preferably an antibody (including fully human, non-human, humanized, or chimeric antibodies) or an antibody fragment (including enzymatically or recombinantly produced fragments) and binding proteins incorporating sequences from antibodies or antibody fragments. The antibodies, fragments, and binding proteins may be multivalent and multispecific or multivalent and monospecific as defined above.

In a preferred embodiment of the present invention, antibodies, such as MAbs, are used that recognize or bind to markers or tumor-associated antigens that are expressed at high levels on target cells and that are expressed predominantly or only on diseased cells versus normal tissues, and antibodies that internalize rapidly. Antibodies useful within the scope of the present invention include MAbs with properties as described above (and show distinguishing properties of different levels of internalization into cells and microorganisms), and contemplate the use of, but are not limited to, in cancer, the following MAbs: LL1 (anti-CD74), LL2 and RFB4 (anti-CD22), RS7 (anti-epithelial glycoprotein-1 (EGP-1)), PAM-4 and KC4 (both anti-MUC1), MN-14 (anti-carcinoembryonic antigen (CEA, also known as CD66e), Mu-9 (anti-colon-specific antigen-p), Immu 31 (an anti-alpha-fetoprotein), TAG-72 (e.g., CC49), Tn, J591 (anti-PSMA (prostate-specific membrane antigen)), G250 (an anti-carbonic anhydrase IX MAb) and L243 (anti-HLA-DR). Other useful antigens that may be targeted using these conjugates include HER-2/neu, BrE3, CD19, CD20 (e.g., C2B8, hA20, 1F5 MAbs) CD21, CD23, CD37, CD45, CD74, CD80, alpha-fetoprotein (AFP), VEGF (e.g.Avastin®, fibronectin splice variant), ED-B (e.g., L19), EGF receptor or ErbB1 (e.g., Erbitux®), ErbB2, ErbB3, placental growth factor (P1GF), MUC1, MUC2, MUC3, MUC4, PSMA, gangliosides, HCG, EGP-2 (e.g., 17-1A), CD37, HLA-DR, CD30, Ia, A3, A33, Ep-CAM, KS-1, Le(y), S100, PSA (prostate-specific antigen), tenascin, folate receptor, Thomas-Friedenreich antigens, tumor necrosis antigens, tumor angiogenesis antigens, Ga 733, IL-2, IL-6, T101, MAGE, insulin-like growth factor (ILGF), migration inhibition factor (MIF), the HLA-DR antigen to which L243 binds, CD66 antigens, i.e. CD66a-d or a combination thereof. The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens are expressed mainly in granulocytes, normal epithelial cells of the digestive tract and tumor cells of various tissues. A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002, incorporated herein by reference.

In another preferred embodiment of the present invention, antibodies are used that internalize rapidly and are then re-expressed, processed and presented on cell surfaces, enabling continual uptake and accretion of circulating conjugate by the cell. An example of a most-preferred antibody/antigen pair is LL1, an anti-CD74 MAb (invariant chain, class II-specific chaperone, Ii). The CD74 antigen is highly expressed on B-cell lymphomas, certain T-cell lymphomas, melanomas and certain other cancers (Ong et al., *Immunology* 98:296-302 (1999)), as well as certain autoimmune diseases.

The diseases that are preferably treated with anti-CD74 antibodies include, but are not limited to, non-Hodgkin's lymphoma, Hodgkin's disease, melanoma, lung cancer, myeloid leukemias, and multiple myeloma. Continual expression of the CD74 antigen for short periods of time on the surface of target cells, followed by internalization of the antigen, and re-expression of the antigen, enables the targeting LL1 antibody to be internalized along with any chemotherapeutic moiety it carries. This allows a high, and therapeutic, concentration of LL1-chemotherapeutic drug conjugate to be accumulated inside such cells. Internalized LL1-chemotherapeutic drug conjugates are cycled through lysosomes and endosomes, and the chemotherapeutic moiety is released in an active form within the target cells.

In another aspect, the invention relates to a method of treating a subject, comprising administering a therapeutically effective amount of a therapeutic conjugate of the preferred embodiments of the present invention to a subject. Diseases that may be treated with the therapeutic conjugates of the preferred embodiments of the present invention include, but are not limited to B-cell malignancies (e.g., non-Hodgkin's lymphoma and chronic lymphocytic leukemia using, for example LL2 MAb; see U.S. Pat. No. 6,183,744), adenocarcinomas of endodermally-derived digestive system epithelia, cancers such as breast cancer and non-small cell lung cancer, and other carcinomas, sarcomas, glial tumors, myeloid leukemias, etc. In particular, antibodies against an antigen, e.g., an oncofetal antigen, produced by or associated with a malignant solid tumor or hematopoietic neoplasm, e.g., a gastrointestinal, lung, breast, prostate, ovarian, testicular, brain or lymphatic tumor, a sarcoma or a melanoma, are advantageously used. Such therapeutics can be given once or repeatedly, depending on the disease state and tolerability of the conjugate, and can also be used optimally in combination with other therapeutic modalities, such as surgery, external radiation, radioimmunotherapy, immunotherapy, chemotherapy, antisense therapy, interference RNA therapy, gene therapy, and the like. Each combination will be adapted to the tumor type, stage, patient condition and prior therapy, and other factors considered by the managing physician.

As used herein, the term "subject" refers to any animal (i.e., vertebrates and invertebrates) including, but not limited to mammals, including humans. The term subject also includes rodents (e.g., mice, rats, and guinea pigs). It is not intended that the term be limited to a particular age or sex. Thus, adult and newborn subjects, as well as fetuses, whether male or female, are encompassed by the term.

In another preferred embodiment, the therapeutic conjugates comprising the Mu-9 MAb of the preferred embodiments of the present invention can be used to treat colorectal, as well as pancreatic and ovarian cancers as disclosed in U.S. application Ser. No. 10/116,116, filed Apr. 5, 2002 and by Gold et al. (*Cancer Res.* 50: 6405 (1990), and references cited therein). In addition, the therapeutic conjugates comprising the PAM-4 MAb of the preferred embodiments of the present invention can be used to treat pancreatic cancer, as disclosed in U.S. Provisional Application Ser. No. 60/388,314, filed Jun. 14, 2002.

In another preferred embodiment, the therapeutic conjugates comprising the RS-7 MAb of the preferred embodiments can be used to treat carcinomas such as carcinomas of the lung, stomach, urinary bladder, breast, ovary, uterus, and prostate, as disclosed in U.S. Provisional Application Ser. No. 60/360,229, filed Mar. 1, 2002 and by Stein et al. (*Cancer Res.* 50: 1330 (1990) and *Antibody Immunoconj. Radiopharm.* 4: 703 (1991)).

In another preferred embodiment, the therapeutic conjugates comprising the anti-AFP MAb of the preferred embodiments can be used to treat hepatocellular carcinoma, germ cell tumors, and other AFP-producing tumors using humanized, chimeric and human antibody forms, as disclosed in U.S. Provisional Application Ser. No. 60/399,707, filed Aug. 1, 2002.

In another preferred embodiment, the therapeutic conjugates comprising anti-tenascin antibodies can be used to treat hematopoietic and solid tumors and conjugates comprising antibodies to Le(y) can be used to treat solid tumors.

In a preferred embodiment, the antibodies that are used in the treatment of human disease are human or humanized (CDR-grafted) versions of antibodies; although murine and chimeric versions of antibodies can be used. Same species IgG molecules as delivery agents are mostly preferred to minimize immune responses. This is particularly important when considering repeat treatments. For humans, a human or humanized IgG antibody is less likely to generate an anti-IgG immune response from patients. Antibodies such as hLL1 and hLL2 rapidly internalize after binding to internalizing antigen on target cells, which means that the chemotherapeutic drug being carried is rapidly internalized into cells as well. However, antibodies that have slower rates of internalization can also be used to effect selective therapy with this invention.

In another preferred embodiment, the therapeutic conjugates of the preferred embodiments can be used against pathogens, since antibodies against pathogens are known. For example, antibodies and antibody fragments which specifically bind markers produced by or associated with infectious lesions, including viral, bacterial, fungal and parasitic infections, for example caused by pathogens such as bacteria, *rickettsia*, mycoplasma, protozoa, fungi, and viruses, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361,544, 4,468,457, 4,444,744, 4,818,709 and 4,624,846, and in Reichert and Dewitz, cited above. In a preferred embodiment, the pathogens are selected from the group consisting of HIV virus causing AIDS, *Mycobacterium tuberculosis, Streptococcus agalactiae*, methicillin-resistant *Staphylococcus aureus, Legionella pneumophilia, Streptococcus pyogenes, Escherichia coli, Neisseria gonorrhosae, Neisseria meningitidis, Pneumococcus, Hemophilis influenzae B, Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reo virus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae*, as disclosed in U.S. Pat. No. 6,440,416.

In a more preferred embodiment, drug conjugates of present invention comprising anti-gp120 and other such anti-HIV antibodies can be used as therapeutics for HIV in AIDS patients; and drug conjugates of antibodies to *Mycobacterium tuberculosis* are suitable as therapeutics for drug-refractive tuberculosis. Fusion proteins of anti-gp120 MAb (anti HIV MAb) and a toxin, such as *Pseudomonas* exotoxin, have been examined for antiviral properties (Van Oigen et al., *J Drug Target,* 5:75-91, 1998)). Attempts at treating HIV infection in AIDS patients failed possibly due to insufficient efficacy or unacceptable host toxicity. The drug conjugates of present invention advantageously lack such toxic side effects of protein toxins, and are therefore advantageously used in treating HIV infection in AIDS patients. These drug conjugates can be given alone or in combination with other antibiotics or therapeutic agents that are effective in such patients when given alone.

In another preferred embodiment, diseases that may be treated using the therapeutic conjugates of the preferred embodiments of the present invention include, but are not limited to immune dysregulation disease and related autoimmune diseases, including Class III autoimmune diseases such as immune-mediated thrombocytopenias, such as acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, Sjögren's syndrome, primary biliary cirrhosis, Hashimoto's thyroiditis, thyrotoxicosis, scleroderma, chronic active hepatitis, rheumatoid arthritis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis, and also juvenile diabetes, as disclosed in U.S. Provisional Application Ser. No. 60/360,259, filed Mar. 1, 2002. Typical antibodies useful in these diseases include, but are not limited to, those reactive with HLA-DR antigens, B-cell antigens (e.g., CD19, CD20, CD21, CD22, CD23, CD4, CD5, CD8, CD14, CD15, CD19, CD20, CD21, CD22, CD23, CD25, CD33, CD37, CD38, CD40, CD40L, CD46, CD52, CD54, CD74, CD80, CD126, B7, MUC1, Ia, HM1.24, and HLA-DR). Since many of these autoimmune diseases are affected by autoantibodies made by aberrant B-cell populations, depletion of these B-cells by therapeutic conjugates involving such antibodies bound with the drugs used in this invention, is a preferred method of autoimmune disease therapy, especially when B-cell antibodies are combined, in certain circumstances, with HLA-DR antibodies and/or T-cell antibodies (including those which target IL-2 as an antigen, such as anti-TAC antibody). In a preferred emodiment, the anti-B-cell, anti-T-cell, or anti-macrophage or other such antibodies of use in the treatment of patients with autoimmune diseases also can be conjugated to result in more effective therapeutics to control the host responses involved in said autoimmune diseases, and can be given alone or in combination with other therapeutic agents, such as TNF inhibitors or TNF antibodies, unconjugated B- or T-cell antibodies, and the like.

In a preferred embodiment, diseases that may be treated using the therapeutic conjugates of the current invention include cardiovascular diseases, such as fibrin clots, atherosclerosis, myocardial ischemia and infarction. Antibodies to fibrin are known and in clinical trials as imaging agents for disclosing said clots and pulmonary emboli, while anti-granulocyte antibodies, such as MN-3, MN-15, NCA95, and CD15 antibodies, can target myocardial infarcts and myocardial ischemia, while anti-macrophage, anti-low-density lipoprotein (LDL), and anti-CD74 (e.g., hLL1) antibodies can be used to target atherosclerotic plaques.

In yet another preferred embodiment, diseases that may be treated using the therapeutic conjugates of the current invention include neurodegenerative diseases characterized by a specific lesions against which a targeting moiety can be used, such as amyloid or beta-amyloid associated with Alzheimer's disease, and which serves as a target for localizing antibodies.

In a preferred embodiment of this invention, a more effective incorporation into cells and pathogens can be accomplished by using multivalent, multispecific or multivalent, monospecific antibodies. Multivalent means the use of several binding arms against the same or different antigen or epitope expressed on the cells, whereas multispecific antibodies involve the use of multiple binding arms to target at least two different antigens or epitopes contained on the targeted cell or pathogen. Examples of such bivalent and bispecific antibodies are found in U.S. patent application 60/399,707, filed Aug. 1, 2002; 60/360,229, filed Mar. 1, 2002; 60/388,314, filed Jun. 14, 2002; and Ser. No. 10/116,116, filed Apr. 5, 2002, all of which are incorporated by reference herein. These multivalent or multispecific antibodies are particularly preferred in the targeting of cancers and infectious organisms (pathogens), which express multiple antigen targets and even multiple epitopes of the same antigen target, but which often evade antibody targeting and sufficient binding for immunotherapy because of insufficient expression or availability of a single antigen target on the cell or pathogen. By targeting multiple antigens or epitopes, said antibodies show a higher binding and residence time on the target, thus affording a higher saturation with the drug being targeted in this invention.

In another preferred embodiment, a therapeutic agent used in combination with the camptothecin conjugate of this invention may comprise one or more isotopes, such as $^{212}$Bi, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, or $^{111}$In. Non-radioactive metals, such as manganese, iron and gadolinium, are useful for nuclear imging or MRI, when used along with the stably tethered structures and carriers described herein, or as direct therapeutics (e.g., when a beta-alpha- or Auger-emitting radionuclude is used, all of which are contemplated as useful herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}$Ra, may be used. Therapeutic agents for use in combination with the camptothecin conjugate of this invention also include, for example, chemotherapeutic drugs such as vinca alkaloids, anthracyclines, epidophyllotoxins, taxanes, antimetabolites, alkylating agents, antibiotics, Cox-2 inhibitors, antimitotics, antiangiogenic and proapoptotic agents, particularly doxorubicin, methotrexate, taxol, other camptothecins, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Another class of therapeutic agents consists of radionuclides that emit α-particles (such as $^{212}$Pb, $^{212}$Bi, $^{213}$Bi, $^{211}$At, $^{223}$Ra, $^{225}$Ac), β-particles (such as $^{32}$P, $^{33}$P, $^{47}$SC, $^{67}$Cu, $^{67}$Cu, $^{67}$Ga, $^{89}$Sr, $^{90}$Y, $^{111}$Ag, $^{125}$I, $^{131}$I, $^{142}$Pr, $^{153}$Sm, $^{161}$Tb, $^{166}$Ho $^{166}$Dy, $^{177}$Lu, $^{186}$Re, $^{188}$Re, $^{189}$Re), or Auger electrons (such as $^{111}$In, $^{125}$I, $^{67}$Ga, $^{191}$Os, $^{193m}$Pt, $^{195m}$Pt, $^{195m}$Hg). Alternatively therapeutic agents may comprise a radioisotope useful for diagnostic imaging. Suitable radioisotopes may include those in the energy range of 60 to 4,000 KeV, or more specifically, $^{18}$F, $^{52}$Fe, $^{62}$Cu, $^{64}$Cu, $^{67}$Cu, $^{67}$Ga, $^{68}$Ga, $^{86}$Y, $^{89}$Zr $^{94m}$Tc, $^{94}$Tc, $^{99m}$Tc, $^{45}$Ti, $^{111}$In, $^{123}$I, $^{124}$I, $^{125}$I, $^{131}$I, $^{154-158}$Gd, $^{177}$Lu, $^{32}$P, $^{188}$Re, and the like, or a combination thereof. See, e.g., U.S. patent application entitled "Labeling Targeting Agents with Gallium-68" (Griffiths, G. L. and W. J. McBride, W. J, U.S. Provisional Application No. 60/342,104) which discloses positron emitters, such as $^{18}$F, $^{68}$Ga, $^{94m}$Tc, and the like, for imaging purposes; incorporated entirely by reference). Detection can be achieved, for example, by single photon emission computed tomography (SPECT), or positron emission tomography (PET). The application also may be for intraoperative diagnosis to identify occult neoplastic tumors. Imaging therapeutic agents may include one or more image enhancing agents, which may include complexes of metals selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

In still other embodiments, a therapeutic agent may comprise one or more radioactive isotopes useful for killing neoplastic or other rapidly dividing cells, which include β-emitters (such as $^{32}P$, $^{33}P$, $^{47}Sc$, $^{67}Cu$, $^{67}Ga$, $^{89}Sr$, $^{90}Y$, $^{111}Ag$, $^{125}I$, $^{131}I$, $^{142}Pr$, $^{153}Sm$, $^{161}Tb$, $^{166}Ho$, $^{166}Dy$, $^{177}Lu$, $^{186}Re$, $^{188}Re$, $^{189}Re$), Auger electron emitters (such as $^{111}In$, $^{125}I$, $^{67}Ga$, $^{191}Os$, $^{193m}Pt$, $^{195m}Pt$, $^{195m}Hg$), α-emitters (such as $^{212}Pb$, $^{212}Bi$, $^{213}Bi$, $^{211}At$, $^{223}Ra$, $^{225}Ac$), or a combination thereof.

Therapeutic agents to be used in concert with the camptothecin conjugates also may be toxins conjugated to targeting moieties. Toxins that may be used in this regard include ricin, abrin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin. (See, e.g., Pastan. et al., Cell (1986), 47:641, and Goldenberg, Calif.—A Cancer Journal for Clinicians (1994), 44:43. Additional toxins suitable for use herein are known to those of skill in the art and are disclosed in U.S. Pat. No. 6,077,499, which is incorporated in its entirety by reference.

In various embodiments, a conjugate as disclosed herein may be part of a composite, multispecific antibody. Such antibodies may contain two or more different antigen binding sites, with differing specificities. The multispecific composite may bind to different epitopes of the same antigen, or alternatively may bind to two different antigens. Some of the more preferred target combinations include the following. This is a list of examples of preferred combinations, but is not intended to be exhaustive.

TABLE 1

Some Examples of multispecific antibodies

| First target | Second target |
|---|---|
| MIF | A second proinflammatory effector cytokine, especially HMGB-1, TNF-α, IL-1, or IL-6 |
| MIF | Proinflammatory effector chemokine, especially MCP-1, RANTES, MIP-1A, or MIP-1B |
| MIF | Proinflammatory effector receptor, especially IL-6R IL-13R, and IL-15R |
| MIF | Coagulation factor, especially TF or thrombin |
| MIF | Complement factor, especially C3, C5, C3a, or C5a |
| MIF | Complement regulatory protein, especially CD46, CD55, CD59, and mCRP |
| MIF | Cancer associated antigen or receptor |
| HMGB-1 | A second proinflammatory effector cytokine, especially MIF, TNF-α, IL-1, or IL-6 |
| HMGB-1 | Proinflammatory effector chemokine, especially MCP-1, RANTES, MIP-1A, or MIP-1B |
| HMGB-1 | Proinflammatory effector receptor especially MCP-1, RANTES, MIP-1A, or MIP-1B |
| HMGB-1 | Coagulation factor, especially TF or thrombin |
| HMGB-1 | Complement factor, especially C3, C5, C3a, or C5a |
| HMGB-1 | Complement regulatory protein, especially CD46, CD55, CD59, and mCRP |
| HMGB-1 | Cancer associated antigen or receptor |
| TNF-α | A second proinflammatory effector cytokine, especially MIF, HMGB-1, TNF-α, IL-1, or IL-6 |
| TNF-α | Proinflammatory effector chemokine, especially MCP-1, RANTES, MIP-1A, or MIP-1B |
| TNF-α | Proinflammatory effector receptor, especially IL-6R IL-13R, and IL-15R |
| TNF-α | Coagulation factor, especially TF or thrombin |
| TNF-α | Complement factor, especially C3, C5, C3a, or C5a |
| TNF-α | Complement regulatory protein, especially CD46, CD55, CD59, and mCRP |
| TNF-α | Cancer associated antigen or receptor |
| LPS | Proinflammatory effector cytokine, especially MIF, HMGB-1, TNF-α, IL-1, or IL-6 |
| LPS | Proinflammatory effector chemokine, especially MCP-1, RANTES, MIP-1A, or MIP-1B |
| LPS | Proinflammatory effector receptor, especially IL-6R IL-13R, and IL-15R |
| LPS | Coagulation factor, especially TF or thrombin |
| LPS | Complement factor, especially C3, C5, C3a, or C5a |
| LPS | Complement regulatory protein, especially CD46, CD55, CD59, and mCRP |
| TF or thrombin | Proinflammatory effector cytokine, especially MIF, HMGB-1, TNF-α, IL-1, or IL-6 |
| TF or thrombin | Proinflammatory effector chemokine, especially MCP-1, RANTES, MIP-1A, or MIP-1B |
| TF or thrombin | Proinflammatory effector receptor, especially IL-6R IL-13R, and IL-15R |
| TF or thrombin | Complement factor, especially C3, C5, C3a, or C5a |
| TF or thrombin | Complement regulatory protein, especially CD46, CD55, CD59, and mCRP |
| TF or thrombin | Cancer associated antigen or receptor |

Still other combinations, such as are preferred for cancer therapies, include CD20+CD22 antibodies, CD74+CD20 antibodies, CEACAM5 (CEA)+CEACAM6 antibodies, insulin-like growth factor (ILGF)+CEACAM5 antibodies, EGP-1 (e.g., RS-7)+ILGF antibodies, CEACAM5+EGFR antibodies. Such antibodies need not only be used in combination, but can be combined as fusion proteins of various forms, such as IgG, Fab, scFv, and the like, as described in U.S. Pat. Nos. 6,083,477; 6,183,744 and 6,962,702 and U.S. Patent Application Publication Nos. 20030124058; 20030219433; 20040001825; 20040202666; 20040219156; 20040219203; 20040235065; 20050002945; 20050014207; 20050025709; 20050079184; 20050169926; 20050175582; 20050249738; 20060014245 and 20060034759, incorporated herein in their entirety by reference.

In certain embodiments, the binding moieties described herein may comprise one or more avimer sequences. Avimers are a class of binding proteins somewhat similar to antibodies in their affinities and specificities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains, which may exhibit improved affinity (in some cases sub-nanomolar) and specificity compared with single-epitope binding proteins. (Id.) In various embodiments, avimers may be attached to, for example, AD and/or DDD sequences for use in the claimed methods and compositions, as described in provisional U.S. Patent Application Ser. Nos. 60/668,603, filed Apr. 6, 2005 and 60/751,196, filed Dec. 16, 2005, each incorporated herein in their entirety by reference. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

Production of Antibody Fragments

Methods of monoclonal antibody production are well known in the art and any such known method may be used to produce antibodies of use in the claimed methods and compositions. Some embodiments of the claimed methods and/or compositions may concern antibody fragments. Such antibody fragments may be obtained by pepsin or papain digestion of whole antibodies by conventional methods. For example, antibody fragments may be produced by enzymatic cleavage of antibodies with pepsin to provide a 5S fragment denoted $F(ab')_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. Exemplary methods for producing antibody fragments are disclosed in U.S. Pat. No. 4,036,945; U.S. Pat. No. 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V^H$ and $V^L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V^H$ and $V^L$ chains connected by a peptide linker. These single-chain antigen binding proteins (sFv) are prepared by constructing a structural gene comprising DNA sequences encoding the $V^H$ and $V^L$ domains, connected by an oligonucleotides linker sequence. The structural gene is inserted into an expression vector that is subsequently introduced into a host cell, such as *E. coli*. The recombinant host cells synthesize a single polypeptide chain with a linker peptide bridging the two V domains. Methods for producing sFvs are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.)

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immun., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990). In another embodiment, an antibody may be a human monoclonal antibody. Such antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994).

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the μ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), 1st edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact. The XenoMouse® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XenoMouseg immunized with a target antigen will produce human antibodies by the normal immune response, which may be harvested and/or produced by standard techniques discussed above. A variety of strains of XenoMouse® are available, each of which is capable of producing a different class of antibody. Such human antibodies may be coupled to other molecules by chemical cross-linking or other known methodologies. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Avimers

In certain embodiments, the precursors, monomers and/or complexes described herein may comprise one or more avimer sequences. Avimers are a class of binding proteins somewhat similar to antibodies in their affinities and specifities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains, that may exhibit improved affinity (in some cases sub-nanomolar) and specificity compared with single-epitope binding proteins. (Id.) In various embodiments, avimers may be attached to, for example, DDD sequences for use in the claimed methods and compositions. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

Phage Display

Certain embodiments of the claimed compositions and/or methods may concern binding peptides and/or peptide mimetics of various target molecules, cells or tissues. Binding peptides may be identified by any method known in the art, including but not limiting to the phage display technique. Various methods of phage display and techniques for producing diverse populations of peptides are well known in the art. For example, U.S. Pat. Nos. 5,223,409; 5,622,699 and 6,068,829, each of which is incorporated herein by reference, disclose methods for preparing a phage library. The phage display technique involves genetically manipulating bacteriophage so that small peptides can be expressed on their surface (Smith and Scott, 1985, Science 228:1315-1317; Smith and Scott, 1993, Meth. Enzymol. 21:228-257).

The past decade has seen considerable progress in the construction of phage-displayed peptide libraries and in the development of screening methods in which the libraries are used to isolate peptide ligands. For example, the use of peptide libraries has made it possible to characterize interacting sites and receptor-ligand binding motifs within many proteins, such as antibodies involved in inflammatory reactions or integrins that mediate cellular adherence. This method has also been used to identify novel peptide ligands that may serve as leads to the development of peptidomimetic drugs or imaging agents (Arap et al., 1998a, Science 279:377-380). In addition to peptides, larger protein domains such as single-chain antibodies may also be displayed on the surface of phage particles (Arap et al., 1998a).

Targeting amino acid sequences selective for a given organ, tissue, cell type or target molecule may be isolated by panning (Pasqualini and Ruoslahti, 1996, Nature 380:364-366; Pasqualini, 1999, The Quart. J. Nucl. Med. 43:159-162). In brief, a library of phage containing putative targeting peptides is administered to an intact organism or to isolated organs, tissues, cell types or target molecules and samples containing bound phage are collected. Phage that bind to a target may be eluted from a target organ, tissue, cell type or target molecule and then amplified by growing them in host bacteria.

In certain embodiments, the phage may be propagated in host bacteria between rounds of panning. Rather than being lysed by the phage, the bacteria may instead secrete multiple copies of phage that display a particular insert. If desired, the amplified phage may be exposed to the target organs, tissues, cell types or target molecule again and collected for additional rounds of panning. Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998a, Smith et al., 1985).

In some embodiments, a subtraction protocol may be used to further reduce background phage binding. The purpose of subtraction is to remove phage from the library that bind to targets other than the target of interest. In alternative embodiments, the phage library may be prescreened against a control cell, tissue or organ. For example, tumor-binding peptides may be identified after prescreening a library against a control normal cell line. After subtraction the library may be screened against the molecule, cell, tissue or organ of interest. Other methods of subtraction protocols are known and may be used in the practice of the claimed methods, for example as disclosed in U.S. Pat. Nos. 5,840,841, 5,705,610, 5,670,312 and 5,492,807, incorporated herein by reference.

Aptamers

In certain embodiments, a targeting moiety of use may be an aptamer. Methods of constructing and determining the binding characteristics of aptamers are well known in the art. For example, such techniques are described in U.S. Pat. Nos. 5,582,981, 5,595,877 and 5,637,459, each incorporated herein by reference. Methods for preparation and screening of aptamers that bind to particular targets of interest are well known, for example U.S. Pat. No. 5,475,096 and U.S. Pat. No. 5,270,163, each incorporated by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In preferred embodiments, the binding sequences of aptamers may be flanked by primer-binding sequences, facilitating the amplification of the aptamers by PCR or other amplification techniques.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)$NR_2$, P(O)R, P(O)OR', CO, or $CNR_2$, wherein R is H or alkyl (1-20C) and R' is alkyl (1-20C); in addition, this group may be attached to adjacent nucleotides through O or S. Not all linkages in an oligomer need to be identical.

Conjugation Protocols

The preferred conjugation protocol is based on a thiol-maleimide, a thiol-vinylsulfone, a thiol-bromoacetamide, or a thiol-iodoacetamide reaction that are facile at neutral or acidic pH. This obviates the need for higher pH conditions for conjugations as, for instance, would be necessitated when using active esters.

Suitable routes of administration of the conjugates of the preferred embodiments of the present invention include, without limitation, oral, parenteral, rectal, transmucosal, intestinal administration, intramuscular, subcutaneous, intramedullary, intrathecal, direct intraventricular, intravenous, intravitreal, intraperitoneal, intranasal, or intraocular injections. The preferred routes of administration are parenteral. Alternatively, one may administer the compound in a local rather than systemic manner, for example, via injection of the compound directly into a solid tumor.

Various embodiments of the present invention are illustrated by the following examples, without limiting the scope thereof.

EXAMPLES

General

The intermediate Phe-Lys(MMT)-PABOH and the cross-linkers Phe-Lys(MMT)-PABOH, MC-Phe-Lys(MMT)-PABOH and MC-Phe-Lys(MMT)-PABOCOO-PNP, where MC is maleimidocaproyl, Phe is phenylalanine, Lys is lysine, MMT is monomethoxytrityl, PABOH is p-aminobenzyl alcohol, and PNP is p-nitrophenyl moiety, were synthesized using a published method (Dubowchik et al., supra). CPT-20-O-acyl derivatives of amino acids were prepared adapting a published method (Vishnuvajjala, supra). In the examples below, the abbreviations noted herein apply. Further, $PEG_{12}$ of Example-3 is maleimide-$PEG_{12}$-NHS ester (see 0041, formula 3), with PEG being polyethyleneglycol. 'AA' in Example-4 is abbreviation for amino acid.

Example 1

Preparation of MC-Phe-Lys-PABOCO-20-O-CPT-10-O-BOC; and the Examination of Selective Removal of BOC Protecting Group 10-Hydroxy-CPT (0.2307 g) was reacted with di-tert-butyl dicarbonate and pyridine under conditions given in Example 2 below to obtain 10-BOC-O-CPT derivative. The latter (24.7 mg) was treated with 4-dimethylaminopyridine (20.7 mg) and triphosgene (5.9 mg) in anhydrous dichloromethane, and the chloroformate so formed was reacted in situ with equimolar amount of MC-Phe-Lys(MMT)-PABOH for a short duration, typically under 5 minutes. Chromatography on silica gel (230-400 mesh) using methanol-dichloromethane gradient led to the isolation of the title product as a closely eluting mixture with some unreacted starting material. Mass spectrum clearly showed the formation of the product (M+Na at m/e 1376). TFA-mediated cleavage for just two-to-five minutes gave the required BOC-removed product, as shown by time-course analyses by thin-layer chromatography in the 1-7½ min duration of the reaction, and by mass spectral data (strong $MH^+$ at m/e 982) of product obtained by the optimized condition. Prolonged TFA-deprotection for 30 minutes led to the cleavage of 20-carbonate bond as well, to form 10-OH-CPT. Thus, selective cleavage of 10-BOC in presence of 20-carbonate by short-duration TFA reaction was accomplished.

Example 2

Preparation of MC-Phe-Lys-PABOCO-20-O-SN-38 ('CL-SN-38')

SN-38 (0.5114 g; 1.305 mmol) was reacted with di-tert-butyl dicarbonate (0.307 g) in anhydrous pyridine (8 mL) for 18 h at ambient temperature. The solvent was evaporated, and the crude material was purified by flash chromatography, on silica gel (230-400 mesh) using methanol-dichloromethane gradient, to obtain 0.55 g of pale yellow solid product of 10-t-butyloxycarbonyl derivative of SN-38, BOC-SN-38. This material (0.0358 g) was dissolved in anhydrous dichloromethane (1.5 mL), and treated with 4-N,N-dimethylaminopyridine (DMAP; 26.6 mg) and triphosgene (0.0095 mg) for 7 minutes, and the chloroformate generated, BOC-SN-38-20-chloroformate, was reacted in situ with MC-Phe-Lys (MMT)-PABOH (0.0754 g) for a short duration, typically under 5 minutes. The reaction mixture was then purified by flash chromatography on silica gel (230-400 mesh) using methanol-dichloromethane gradient. Yield: 42.4 mg. A portion of this product (21.9 mg) was treated with a mixture of trifluoroacetic acid ("TFA"; 1 mL), dichloromethane (0.25 mL), and anisole (0.14 mL) for a few minutes, typically less than five minutes, and the product was isolated by precipitation with diethyl ether. TFA-treatment was optionally repeated 2 or 3 more additional times, each for a short-duration of less than five minutes. Analysis by reverse phase HPLC ($C_{18}$ column, gradient elution using solution A changing to solution 'B' in 10 minutes at 3 mL/min, then maintained at 100% 'B' for 5 min.; 'A': 0.3% aq. ammonium acetate, pH 4.43; 'B': 9:1 $CH_3CN$/0.3% aq ammonium acetate, pH 4.43) showed a peak 10.796 min (absorbance at 360 nm) due to the title compound, which was usually 76%-83%, with most of the remainder being SN-38. Further purification gives rise to product with 90% purity, the remainder being SN-38. The final product, with these levels of purity, is used for conjugation to antibodies. Electrospray mass spectrum showed mass peak at m/e 1009 in the negative ion mode (M-H) and a strong peak at m/e 1011 in the positive ion mode, attributable to the title compound.

Example 3

Preparation of maleimido-$PEG_{12}$-Phe-Lys-PAB-OCO-20-O-SN-38 ('PEG-CL-SN-38')

Maleimido-$PEG_{12}$ moiety was substituted for maleimidocaproyl of Example 2 using commercially available heterobifunctional cross-linker, maleimide-$PEG_{12}$-NHS ester (see 0040, formula 3), by reacting the intermediate Phe-Lys (MMT)-PABOH in DMF and diisopropylethylamine, to generate the cross-linker maleimide-$PEG_{12}$-Phe-Lys(MMT)-PABOH. Here $PEG_{12}$ is a defined PEG substrate containing 12 monomeric units, and was used to increase the solubility of drug-linker intermediate under MAb conjugation conditions. The cross-linker, maleimido-$PEG_{12}$-Phe-Lys(MMT)-PABOH, was reacted with BOC-SN-38 20-chloroformate of Example 2. Experimental conditions and purifications were analogous to that detailed in Example 2. The product was subjected to TFA-mediated deprotection to obtain the title product. Electrospray mass spectrum showed peak at m/e 1602 (M+Cl) and 1681 (M+TFA) in the negative ion mode and a strong peak at m/e 1568 (M+H) in the positive ion mode, attributable to the title compound.

Example 4

Preparation of MC-Phe-Lys-PABOCO-AA-20-O-SN-38 ('CL-AA-SN-38')

The general formula of the product is given in formula 13. BOC-SN-38 of Example 2 was esterified at the 20-hydroxyl position using BOC-glycine, MMT-glycine, BOC-sarcosine, or BOC-alanine. The general procedure involved reacting BOC-SN-38 with 20% molar excess each of amine-protected amino acid (AA) and dicyclohexylcarbodiimide in anhydrous dichloromethane, in presence of catalytic amount of 4-dimethylaminopyridine, in a overnight reaction at ambient temperature. The esterified product, purified by flash chromatography, was treated with dichloroacetic acid (DCA) to remove just the MMT group, or with TFA to remove the protecting group on both the amine terminus of the ester and the BOC group on SN-38. The SN-38 derivative containing C-20 ester, with amine terminus present as TFA or DCA salt, and with 10-hydroxyl protected or free, was then reacted with ~10% molar excess of MC-Phe-Lys(MMT)-PABOCOO-PNP (for description, see General section under EXAMPLES) and DIEA in DMF. Purification by flash chromatography furnished the penultimate intermediate in each case, which was reacted with TFA to obtain the title materials. Title compounds: With glycinate at C-20 ($R_1$=$R_2$=H in the structure): mass spectrum, M−H at m/e 1065; with sarcosinate at C-20 ($R_1$=methyl; $R_2$=H in the structure): mass spectrum M+H at m/e 1081 (positive ion mode) and M−H at m/e 1079 (negative ion mode); with alanate at C-20 ($R_1$=H; $R_2$=methyl in the structure): mass spectrum, M+Na at m/e 1662, M−H at m/e 1638 in positive and negative ion modes, respectively.

(13)

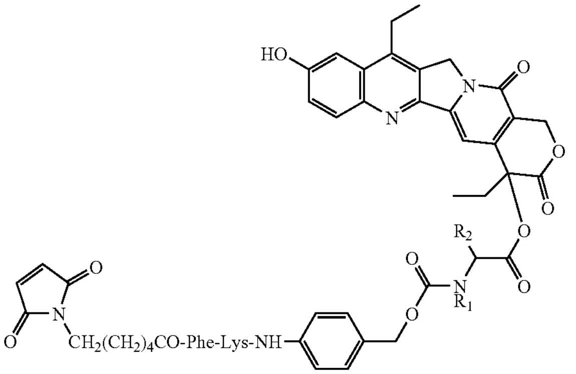

Example 5

Preparation of HS—$(CH_2)_2$—CO-Phe-Lys-PAB-OCO-20-O—SN-38 ('CLS-SN-38')

Succinimidyl S-methoxytritylthiopropionate was prepared in 2 steps from thiopropionic acid by reacting the latter with a molar equivalent of MMT chloride in anhydrous dichloromethane containing 2.5 equivalents of diisopropylethyamine (DIEA), with MMT being abbreviation for monomethoxytrityl. After the reaction was complete, as monitored by thin-layer chromatography, the reaction mixture was diluted with ethyl acetate, and washed with water and saturated sodium chloride. The product, purified by flash chromatography, was converted to its succinimidyl ester with equimolar amounts of N-hydroxysuccinimide and dicyclohexylcarbodiimide in DMF. The precipitated DCC-urea was filtered off, and the filtrate was used as such for reaction with the intermediate Phe-Lys(MMT)-PABOH (see General section under 'EXAMPLES') in DMF using equimolar amounts of the reactants as well as DIEA. The required product was isolated by flash chromatography. The product, MMT-S—$(CH_2)_2$—CO-Phe-Lys(MMT)-PABOH, was obtained in 84.7% yield. Its electrospray mass spectrum showed M+H at m/e 1032 and a strong M+Na at m/e 1054 in the positive ion mode, and M−H peak at m/e 1030 in the negative ion mode, as expected for its structure. This material was reacted with BOC-SN-38-(20)-chloroformate and the product was purified in a manner analogous to that detailed in Example 2, to obtain the product MMT-S—$(CH_2)_2$—CO-Phe-Lys-PAB-OCO-(20)—SN-38-(10)-BOC. Its mass spectrum was consistent with the structure (M+Na at m/e 1572, M−H at m/e 1548, M+TFA at m/e 1663). Finally, short-duration treatment with TFA, as described in Example 2, furnished the title product, of >87% purity by HPLC with ~5% of SN-38 as a by-product. Its mass spectrum showed M+H at m/e 906 and M−H at m/e 904, in the positive and negative ion modes, respectively.

Example 6

Conjugation of Maleimide-Containing SN-38 Intermediates to Mildly Reduced Antibodies: Attachment to Interchain Region of MAbs The anti-CD22 humanized MAb, hLL2, the anti-CD74 humanized MAb, hLL1, the anti-EGP-1 humanized MAb, hRS7, and anti-IGFR1 chimeric MAb, cR1, were used in these studies. Each antibody was reduced with dithiothreitol (DTT), used in a 50-to-70-fold molar excess, in 40 mM PBS, pH 7.4, containing 5.4 mM EDTA, at 37° C. (bath) for 45 min. The reduced product was purified on centrifuged size-exclusion column and buffer-exchanged with 75 mM sodium acetae-1 mM EDTA. The thiol content was determined by Ellman's assay, and was in the 6.5-to-8.5 SH/IgG range. The reduced MAb was reacted with 12.5-to-22.5-fold molar excess of 'CL-SN-38' of Example 2, or 'PEG-CL-SN-38' of Example 3, or 'CL-AA-SN-38' of Example 4, using DMF at 5-10% v/v as co-solvent, and incubating for 20 min at ambient temperature. The conjugate was purified by centrifuged SEC, passage through a hydrophobic column, and finally by ultrafiltration-diafiltration. The product was assayed for SN-38 by absorbance at 366 nm and correlating with standard values, while the protein concentration was deduced from absorbance at 280 nm, corrected for spillover of SN-38 absorbance at this wavelength. This way, the SN-38/MAb substitution ratios were determined. The purified conjugates were stored as lyophilized formulations in glass vials, capped under vacuum and stored in a −20° C. freezer. SN-38 molar substitution ratios (MSR) obtained for some of these conjugates, which are typically in the 5-to-8 range in view of the mode of conjugation, are shown in Table 2.

Example 7

Conjugation of CLS-SN-38 to Maleimide-Appended Antibodies: Attachment to Lysine Side Chain of MAbs The anti-CD22 humanized MAb, hLL2 and the anti-EGP-1 humanized MAb, hRS7 were examined in these studies. Each antibody was derivatized with7-to-10-fold molar excess of sulfo-SMCC in PBS, pH 7.4, at 4° C. for 40 min. The conjugate in each case was purified by centrifuged SEC and buffer exchanged with 75 mM sodium acetate-1 mM EDTA, pH 6.5, diluted to 5 mg/mL, and the pH was adjusted to pH 5 with acetic acid. The maleimide-added antibody was then reacted with a slight molar excess (~1.15 equivalent with respect to each maleimide group on the antibody) of 'CLS-SN-38' of Example 5, with DMF used as co-solvent at ~10% v/v. After 15 min at ambient temperature, the conjugates were purified and the SN-38 molar substitutions were determined as described for conjugates of Example 6. SN-38 substitution obtained for some of these conjugates, in which the drug is attached to lysine amino groups of MAbs, are shown in Table 2 (entries italicized); drug substitutions are typically lower in these than in conjugates of Example 6.

TABLE 2

SN-38/MAb Molar substitution ratios (MSR) in some conjugates

| MAb | Conjugate | MSR |
|---|---|---|
| hLL1 | hLL1-[CL-SN-38], using drug-linker of example 2 | 8.2 |
| | hLL1-[PEG-CL-SN-38], using drug-linker of example 3 | 5.9 |
| | hLL1-[CL-Gly-SN-38], using drug-linker of example 4 (AA = Gly) | 6.7 |
| | hLL1-[CL-Sar-SN-38], using drug-linker of 4 (AA = Sar) | 7.8 |
| hLL2 | hLL2-[CL-SN-38], using drug-linker of example 2 | 8.6 |
| | hLL2-[PEG-CL-SN-38], using drug-linker of example 3 | 5.4 |
| | HLL2-[CLS-SN-38], using drug-linker of example 5: 'lysine mode' | 1.5 |
| hRS7 | hRS7-[CL-SN-38], using drug-linker of example 2 | 7.4 |
| | hRS7-[CL-Gly-SN-38], using drug-linker of example 4, AA = Gly | 7.1 |
| | hRS7-[CL-Gly-SN-38], using drug-linker of example 4, AA = Sar | 7.8 |
| | hRS7-[CLS-SN-38], using drug-linker of example 5: 'lysine mode' | 7.5 |
| cR1 | cR1-[PEG-CL-SN-38], using drug-linker of example 3 | 6.0 |

Example 8

In vitro Cytotoxicity of Antibody-SN-38 Conjugates in Lymphoma

Raji B-lymphoma cells were obtained from American Type Culture Collection (ATCC, Rockville, Md.). The SN-38 conjugates were prepared from disulfide-reduced anti-CD74 MAb, hLL1, or the negative control MAb anti-EGP-1 MAb, hRS7, used as control, and had the following compositions: hLL1(or hRS7)-[succinimidocaproyl (abbreviated as SC)]-CL-SN-38 and hLL1 (or hRS7)-[succinimido-$PEG_{12}$ (abbreviated as S-$PEG_{12}$)]-CL-SN-38, where CL is Phe-Lys-PAB-OCO moiety, with PAB derived from p-aminobenzyl. The lyophilized conjugates were reconstituted with saline to 5 mg/mL. Other controls included unmodified hLL1 and SN-38 (DMSO solution). Cells were harvested and plated into 96 well plates (25,000 cells/well). 20 μL of serially diluted solutions of conjugates or controls were added to each well to final concentration of 0-7 μM final concentration of SN-38 equivalent, and incubated at 37° C. The media was discarded either at 4 h or 48 h time-point, with washings followed by addition of fresh media. Total incubation time was 48 h. MTS dye reduction assay was used to determine dose response curves, and effective $EC_{50}$ concentrations were determined using PrismPad® Software (Advanced Graphics Software, Encinitas, Calif.). Table 3 below shows the specific cytotoxicity due to hLL1 conjugates.

Table 3: EC50 Values (in drug equivalents) calculated for MAb-SN-38 conjugates against Raji Burkitt's lymphoma, at 4-hr and 48-hr exposure (N/A: not applicable)

| Conjugate | Type | 4 hr | 48 hr |
|---|---|---|---|
| hLL1-[SC-CL]-SN-38 | Specific | 35 nM | 0.33 nM |
| hRS7-[SC-CL]-SN-38 | Non-specific | 835 nM | 5.70 nM |
| hLL1-[S-$PEG_{12}$-CL]-SN-38 | Specific | 117 nM | 0.75 nM |
| hRS7-[S-$PEG_{12}$-CL]-SN-38 | Non-specific | 383 nM | 3.79 nM |
| SN-38 free drug | N/A | 10 nM | 0.93 nM |

In a different experiment, hLL1 and hRS7 conjugates of bifunctional SN-38 derived from SN-38-20-glycinate or SN-38-20-sarcosinate were evaluated in vitro using Raji cells as described above. Specific substrates used were: hLL1-[SC-Phe-Lys-PABOCO-Gly-SN-38] and hLL1-[SC-Phe-Lys-PABOCO-Sar-SN-38], and the non-specific substrates were hRS7-[SC-Phe-Lys-PABOCO-Gly-SN-38] and hRS7-[SC-Phe-Lys-PABOCO-Sar-SN-38]. The abbreviations SC, PAB are as described above, and Phe, Lys, Gly, and Sar are amino acids. Table 4 shows specific cytotoxicity due to these hLL1 conjugates.

TABLE 4

EC50 Values (in drug equivalents) calculated for MAb-SN-38 conjugates against Raji Burkitt's lymphoma, at 4-hr and 48-hr exposure

| Conjugate | Type | 4 hr | 48 hr |
|---|---|---|---|
| hLL1-[SC-Phe-Lys-PABOCO-Gly]-SN-38 | Specific | 70 nM | 1.4 nM |
| hRS7-[SC-Phe-Lys-PABOCO-Gly]-SN-38 | Non-specific | 210 nM | 12 nM |
| hLL1-[SC-Phe-Lys-PABOCO-Sar]-SN-38 | Specific | 240 nM | 7 nM |
| hRS7-[SC-Phe-Lys-PABOCO-Sar]-SN-38 | Non-specific | 360 nM | 31 nM |

Example 9

In vivo Therapy of Raji Systemic Lymphoma in Severe Combined Immunodeficient (SCID) Mice with hLL1-SN-38 Derivatives The conjugates evaluated were derived from anti-CD74 MAb, hLL1, and had the structures of: hLL1-[succinimidocaproyl (abbreviated as SC)]-CL-SN-38 and hLL1-[succinimido-$PEG_{12}$ (abbreviated as S-$PEG_{12}$)]-CL-SN-38, where CL is Phe-Lys-PABOCO moiety, with PAB derived from p-aminobenzyl, and Phe and Lys being amino acids phenylalanine and lysine, respectively. 8-Week old female SCID mice were inoculated with $2.5\times10^6$ Raji cells i.v. On the following day, 500 μg of test agents or unmodified hLL1 antibody was injected i.v. into groups of 5 mice. The animals were monitored daily for signs of disease progression which is hind-limb paralysis and/or >20% body weight loss. Mice treated with either conjugate are alive beyond a median survival at 125 days, compared to median survival of 56 days for treatment with unmodified antibody. Further, hLL1-[SC-CL]-SN-38 ("hLL1-CL-SN-38") was significantly better than the antibody-alone control (P<0.0064). These data demonstrated the therapeutic efficacies obtained with these conjugates.

Example-10

In vivo Therapy of Daudi Systemic Lymphoma in Severe Combined Immunodeficient (SCID) Mice Targeted with anti-CD22 hLL2-SN-38 Drug Conjugate 8-Week old female SCID mice were inoculated with $1.5\times10^7$ Daudi cells i.v. On the following day, 100, 200, or 500 μg of hLL2-SN-38 was injected, and this regimen was followed twice weekly for 3 weeks and once in the 4$^{th}$ week. The controls consisted untreated mice as well as those receiving the equivalent doses of unmodified hLL2. Eight animals per group were used. The animals were monitored daily for signs of disease progression which is hind-limb paralysis and/or >20% body weight loss. Median survival of 500 μg-dose, 200 μg-dose, and 100 μg-dose groups, with median survivals for the respective equivalent naked hLL2 dose groups given in parentheses, were >98 days (49.5 days), 92.5 days (54.5 days), 74.5 days (42 days), respectively. Untreated animals succumbed on day 27. For the highest dose group, median survival was not yet reached on day 98, as 7 of 8 mice were alive. These data demonstrated the therapeutic efficacy of the anti-CD22 hLL2-SN-38 conjugate.

Example-11

Elimination of HIV Infection by Treatment with a SN-38 Conjugate of an anti-gp120 MAb A MAb targeted to the HIV envelope protein gp120, anti-gp120 antibody such as P4/D10, is reduced using conditions described in Example 5, and the reduced MAb is reacted with a 20-fold molar excess of the drug linker CL-SN-38, which is as described for Example 1. An anti-gp120-SN-38 conjugate with a substitution of 8 drug molecules per antibody is obtained. An in vitro HIV-inhibition assay with said conjugate is performed by using various mixtures of uninfected Jurkat-T cells and fully HIV-infected Jurkat T-cells (in the ratios of 99.8:2 to 95:5), and treating with serial dilutions of the conjugate, non-specific hRS7-CL-SN38 conjugate control, naked antibody, and HIV-negative serum from 100 to 0.00001 μg/mL. The cells so treated are incubated in RPMI 1640 culture medium at 37° C. for seven days, and then assayed for HIV inhibition by the relevant ELISA test. This experiment shows a strong and specific inhibition of intercellular spread of HIV by the specific drug conjugate. The in vivo efficacy is tested by administering mice with isologous HIV-infected cells together with specific and non-specific SN-38 conjugates. For this, primary murine splenocytes infected by HIV-1/MuLV pseudotype virus are intraperitoneally transferred to groups of mice simultaneously with immunoconjugate administration. Peritoneal cells are harvested 10 days later. While infectious HIV presence is demonstrated in control mice, no infectious HIV is detected in mice treated with 100 μg or less of anti-gp120-SN-38 conjugate. No protection is seen with mice treated with control conjugates.

From the foregoing description, one skilled in the art can easily ascertain the essential characteristics of this invention, and without departing from the spirit and scope thereof, can make various changes and modifications of the invention to adapt it to various usage and conditions without undue experimentation. All patents, patent applications and publications cited herein are incorporated by reference in their entirety.

What is claimed is:

1. A conjugate of a camptothecin drug and a targeting moiety (TM) of the formula: TM-[L]-CPT, where TM is a cancer targeting monoclonal antibody; CPT is selected from the consisting of camptothecin, 10-hydroxy camptothecin, SN-38, topotecan, lurtotecan, 9-aminocamptothecin, and 9-nitrocamptothecin; and L is a linker system of the type X-Y-Z wherein X is an antibody coupling moiety comprising a defined polyethylene glycol (PEG) wherein the defined PEG contains a defined number of monomeric units that is between 1 and 12 monomeric units, Y is a lysosomally cleavable polypeptide, and Z is 4-aminobenzyloxy moiety, which is connected to the CPT drug, wherein Z is connected to a 20-hydroxy group of CPT by a carbonate or carbamate bond and X is connected to TM by a bond between a thiol group and a thiol-reactive moiety selected from the group consisting of maleimide, vinylsulfone, bromoacetamide, and iodoacetamide.

2. The conjugate according to claim 1, wherein the antibody is a chimeric antibody or a humanized antibody.

3. The conjugate according to claim 1, wherein X is an antibody coupling moiety comprising a defined polyethylene glycol (PEG) with 12 monomeric units.

4. The conjugate according to claim 1, wherein the antibody is a human antibody.

5. The conjugate according to claim 1, wherein the monoclonal antibody is part of a bi-specific or multi-specific antibody.

6. The conjugate according to claim 5, wherein the monoclonal antibody is part of a trivalent, bi-specific antibody complex.

7. The conjugate according to claim 1, wherein said CPT is SN-38.

8. The conjugate according to claim 1, wherein the cleavable polypeptide is selected from the group consisting of Phe-Lys, Val-Cit, Ala-Leu, and Leu-Ala-Leu.

9. The conjugate according to claim 1 wherein 'Z' is connected via a carbonate bond to the 20-hydroxy group of CPT.

10. A process for producing the conjugate of claim 1, wherein the linker is first conjugated to the CPT drug, thereby producing a CPT drug-linker conjugate, wherein said CPT drug-linker conjugate is subsequently conjugated to a monoclonal antibody, wherein the CPT comprises a 10-hydroxyl group that is a t-butyloxycarbonyl (BOC) derivative and the CPT further comprises a 20-hydroxyl group that is a carbonate derivative and the process comprises exposing the derivatized CPT to trifluoroacetic acid (TFA), wherein the TFA removes the BOC from the 10-hydroxyl position but does not remove the carbonate from the 20-hydroxyl position.

11. The process of claim 10 wherein the derivatized CPT is exposed to TFA for two to five minutes.

12. The process of claim 11, wherein the CPT is SN-38.

13. The process of claim 11, wherein said CPT drug-linker is not purified prior to conjugation to a monoclonal antibody or fragment.

14. The conjugate according to claim 1, wherein said antibody is attached to between 1 and 12 CPT moieties.

15. The conjugate according to claim 14, wherein said antibody is a murine, chimeric, primatized, humanized, or human monoclonal antibody, and said antibody is in intact, fragment (Fab, Fab', F(ab)2, F(ab')2), or sub-fragment (single-chain constructs) form.

16. The conjugate according to claim 15, wherein said antibody is a chimeric antibody.

17. The conjugate according to claim 15, wherein said antibody is a humanized antibody.

18. The conjugate according to claim 1, wherein said antibody binds to a B-cell lineage antigen, a T-cell antigen, a myeloid lineage antigen or a HLA-DR antigen.

19. The conjugate according to claim 18, wherein said antibody binds to a CD20 antigen.

20. The conjugate according to claim 1, wherein said antibody binds to an antigen selected from the group consisting of CD74, CD22, epithelial glycoprotein-1, carcinoembryonic antigen (CEA or CD66e), colon-specific antigen-p, alpha-fetoprotein, CC49, prostate-specific membrane antigen, carbonic anhydrase IX, HER-2/neu, EGFR (ErbB1), ErbB2, ErbB3, ILGF, BrE3, CD19, CD20, CD21, CD23, CD33, CD45, CD74, CD80, VEGF, ED-B fibronectin, P1GF, other tumor angiogenesis antigens, MUC1, MUC2, MUC3, MUC4, gangliosides, HCG, EGP-2, CD37, HLA-DR, CD30, Ia, A3, A33, Ep-CAM, KS-1, Le(y), S100, PSA, tenascin, folate receptor, Thomas-Friedreich antigens, tumor necrosis antigens, Ga 733, IL-2, IL-6, T101, MAGE, migration inhibition factor (MIF), an antigen that is bound by L243, an antigen that is bound by PAM4, CD66a (BGP), CD66b (CGM6), CD66c (NCA), CD66d (CGM1), and TAC.

21. The conjugate of claim 1, wherein said conjugate is in a form suitable for parenteral administration.

22. The conjugate of claim 1, wherein the monoclonal antibody is part of a composite, multispecific antibody.

23. The conjugate of claim 22, wherein the composite antibody binds to two or more antigens selected from the group consisting of CD74, CD22, epithelial glycoprotein-1, carcinoembryonic antigen (CEA or CD66e), colon-specific antigen-p, alpha-fetoprotein, CC49, prostate-specific membrane antigen, carbonic anhydrase IX, HER-2/neu, BrE3, CD19, CD20, CD21, CD23, CD33, CD45, CD74, CD80, VEGF, EGF receptor (ErbB1), ErbB2, ErbB3, P1GF, VEGF, ED-B fibronectin, MUC1, MUC2, MUC3, MUC4, ILGF, gangliosides, HCG, EGP-2, CD37, HLA-DR, CD30, Ia, A3, A33, Ep-CAM, KS-1, Le(y), S100, PSA, tenascin, folate receptor, Thomas-Friedreich antigens, tumor necrosis antigens, tumor angiogenesis antigens, MIF, Ga 733, IL-2, IL-6, T101, MAGE, an antigen that is bound by L243, an antigen that is bound by PAM4, CD66a (BGP), CD66b (CGM6), CD66c (NCA), CD66d (CGM1) and TAC.

24. The conjugate of claim 22, wherein the composite antibody binds to CD20 and CD22.

25. The conjugate of claim 22, wherein the composite antibody contains at least one binding site for EGP-1.

26. The conjugate of claim 22, wherein the composite antibody contains at least one binding site for CD74.

27. The conjugate of claim 1, wherein the antibody is a fusion protein.

28. The conjugate of claim 27, further comprising a second fusion protein, antibody or antibody fragment.

29. The conjugate of claim 28, wherein the second fusion protein, antibody or antibody fragment is also linked to one or more CPT moieties.

30. The conjugate of claim 27, wherein said fusion protein comprises a murine, chimeric, primatized, humanized, or human monoclonal antibody, and said antibody is in intact, fragment (Fab, Fab', F(ab).sub.2, F(ab').sub.2), or sub-fragment (single-chain constructs) form.

31. The conjugate of claim 28, wherein the two fusion proteins bind to the same epitope, to different epitopes on the same antigen or to different antigens.

* * * * *